United States Patent [19]

Kovesdi et al.

[11] Patent Number: 5,851,806
[45] Date of Patent: Dec. 22, 1998

[54] COMPLEMENTARY ADENOVIRAL SYSTEMS AND CELL LINES

[75] Inventors: Imre Kovesdi, Rockville; Douglas E. Brough, Olney; Duncan L. McVey, Derwood; Joseph T. Bruder, Gaithersburg; Alena Lizonova, Rockville, all of Md.

[73] Assignee: GenVec, Inc., Rockville, Md.

[21] Appl. No.: 572,126

[22] Filed: Dec. 14, 1995

Related U.S. Application Data

[63] Continuation-in-part of PCT/US95/07341 Jun. 7, 1995, published as WO96/03837 which is a continuation-in-part of Ser. No. 258,416, Jun. 10, 1994.

[51] Int. Cl.$^6$ .......................... C12P 19/34; C12N 15/11; C12N 5/16; C12N 5/22
[52] U.S. Cl. .................................. 435/91.41; 435/320.1; 435/325; 435/366; 536/24.2
[58] Field of Search ................... 435/69.1, 91.1, 435/235.1, 246.1, 320.1, 91.41, 172.3, 325, 366; 536/23.1, 24.1, 24.2

[56] References Cited

U.S. PATENT DOCUMENTS 4,405,712   9/1983   Vande Woude .............................. 435/5

FOREIGN PATENT DOCUMENTS

| | | |
|---|---|---|
| 94/68503 | 12/1994 | Australia . |
| 94/72646 | 1/1995 | Australia . |
| 2117668 | 9/1995 | Canada . |
| WO 94/28152 | 8/1994 | France . |
| 2 707 664 | 1/1995 | France . |
| WO 94/08026 | 4/1994 | WIPO . |
| WO 94/11506 | 5/1994 | WIPO . |
| WO 94/12649 | 9/1994 | WIPO . |
| PCT/US95/ 14793 | 11/1994 | WIPO ................................ 424/78.08 |
| WO 94/28938 | 12/1994 | WIPO . |
| WO 95/00655 | 1/1995 | WIPO . |

OTHER PUBLICATIONS

Brough et al., *Virology*, 190, 624–634 (1992).
Fallaux et al., *Human Gene Therapy*, 7, 215–222 (1996).
Graham et al., *J. Gen. Virol.*, 36, 59–72 (1977).
Imler et al., *Gene Therapy*, 3, 75–84 (1996).
Klessig et al., *Molecular and Cellular Biology*, 4(7), 1354–1362 (1984).
Kreeger, *The Scientist*, 13, (Feb. 19, 1996).
Krougliak et al., *Human Gene Therapy*, 6, 1575–1586 (1995).
Schaack et al., *J. Virol.*, 4079–4085 (1995).
Wang et al., *Gene Therapy*, 2, 775–783 (1995).
Weinberg et al., *Proc. Natl. Acad. Sci.*, 80, 5383–86 (1983).
Yeh et al., *J. Virol.*, 70(1), 559–565 (1996).
Barr et al., "Efficient Catheter–Mediated Gene Transfer Into The Heart Using Replication–Defective Adenovirus," *Gene Therapy*, 1:51–58 (1994).
Berkner et al., "Generation of Adenovirus By Transfection of Plasmids," *Nucleic Acids Research*, 1117:6003–6020 (1983).
Boucher et al., "Gene Therapy For Cystic Fibrosis Using El–Deleted Adenovirus: A Phase I Trial In The Nasal Cavity," *Human Gene Therapy*, 5:615–639 (1994).
Brough et al., "Construction, Characterization, and Utilization of Cell Lines Which Inducibly Express the Adenovirus DNA–Binding Protein," *Virology*, 190:624–634 (1992).
Davidson et al., "Overproduction of Polyomavirus Middle T Antigen in Mammalian Cells Through the Use of an Adenovirus Vector," *Journal of Virology*, 61(4):1226–1239 (1987).

(List continued on next page.)

*Primary Examiner*—David Guzo
*Assistant Examiner*—William Sandals
*Attorney, Agent, or Firm*—Leydig, Voit & Mayer, Ltd.

[57] ABSTRACT

The present invention provides multiply replication deficient adenoviral vectors having a spacer in at least one replication deficient adenoviral region, as well as complementing cell lines therefor. Also provided are means of constructing the multiply replication deficient adenoviral vectors and methods of use thereof, e.g., in gene therapy.

63 Claims, 17 Drawing Sheets

OTHER PUBLICATIONS

Engelhardt et al., "Adenovirus–Mediated Transfer of the CFTR Gene to Lung of Nonhuman Primates: Biological Efficacy Study," *Humna Gene Therapy*, 4:759–769 (1993).

Klessing et al., "Introduction, Stable Intergration, and Controlled Expression of a Chimeric Adenovirus Gene Whose Product Is Toxic to the Recipient Human Cell," *Molecular and Cellular Biology*, 4(7):1354–1362.

Weinberg et al., "A Cell Line that Supports the Growth of a Defective Early Region 4 Deletion Mutant of Human Adenovirus Type 2," *Proc. Natl. Acad. Sci. USA*, 80:5383–5386 (1983).

Yang et al., "Cellular Immunity to Viral Antigens Limits El–Deleted Adenoviruses for Gene Therapy," *Proc. Natl. Acad. Sci. USA*, 91:4407–4411 (1994).

Armentano et al., "Characterization of an Adenovirus Gene Transfer Vector Containing an E4 Deletion," *Human Gene Therapy* 6:1343–1353 (1995).

Berkner, "Development of Adenovirus Vectors for the Expression of Heterologous Genes," *BioTechniques*, vol. 6, No. 7, 616–629 (1988).

Bout et al., "Lung Gene Therapy: In Vivo Adenvirus–Mediated Gene Transfer to Rhesus Monkey Airway Epithelium," *Human Gene Therapy* 5:3–10 (1994).

Brough et al., "Multiple Functions of the Adenovirus DNA–Binding Protein Are Required for Efficient Viral DNA Synthesis," *Virology*, 196:269–281 (1993).

Crystal et al., "Administration of an adenovirus containing the human cFTR cDNA to the respiratory tract of individuals with cystic fibrosis," *Nature Genetics*, vol. 8, (Sep. 1994).

Gilardi et al., "Expression of human $\alpha_1$–antitrypsin using a recombinant adenvirus vector," *FEBS*, vol. 267, No. 1, 60–62 (Jul. 1990).

Lemarchand et al., "Adenovirus–mediated transfer of a recombinant human $\alpha_1$–antitrypsin cDNA to human endothelial cells," *Proc. Natl. Acad. Sci. USA*, vol. 89, pp. 6482–6486, (Jul. 1992).

Mastrangeli et al., "Diversity of Airway Epithelial Cell Targets for In Vivo Recombinant Adenovirus–mediated Gene Transfer," *The Journal of Clinical Investigation, Inc.*, vol. 91, 225–234 (Jan. 1993).

Mittereder et al., "In Vivo Evaluation of the Safety if Adenovirus–Medicated Transfer of the Human Cystic Fibrosis Transmembrane Conductance Regulator cDNA to the Lung," *Human Gene Therapy* 5:731–744 (1994).

Mittereder et al., "Evaluation of the Efficacy and Safety of In Vitro, Adenovirus–Mediated Transfer of the Human Cystic Fibrosis Transmembrane Conductance Regulator cDNA," *Human Gene Therapy* 5:717–729 (1994).

Morin et al., "Nuclear Localization of the Adenovirus DNA–Binding Protein: Requirement for TWo Signals and Complementation during Viral Infection," *Molecular and Cellular Biology*, pp. 4372–4380 (Oct. 1989).

Rosenfeld et al., "In Vivo Transfer of the Human Cystic Fibrosis Transmembrane Conductance Regulator Gene to the Airway Epithelium," *Cell*, vol. 68, 143–155 (Jan. 10, 1992).

Simon et al., "Adenovirus–Mediated Transfer of the CFTR Gene To Lung of Nonhuman Primates: Toxicity Study," *Human Gene Therapy* 4:771–780 (1993).

Simon et al., "Adenovirus–Mediated Transfer of the CFTR Gene to Lung of Nonhuman Primates: Toxicity Study," *Human Gene Therapy* 4:771–780 (1993).

Trapnell et al., "Gene therapy using adenoviral vectors," *Current Opinion in Biotechnology*, 5:617–625 (1994).

Vos et al., "Charaterization of Adenovirus Type 5 Insertion and Deletion Mutants Encoding Altered DNA Binding Proteins," *Virology* 172:634–642 (1989).

Yang et al., "Inactivation of E2a in recombinant adenoviruses improves the prospect for gene therapy in cystic fibrosis," *Nature Genetics*, vol. 7 pp. 362–369, (Jul. 1994).

Cleghon et al., *J. Virology*, 63, 2289–2299 (1989).

Rice et al., *Virology*, 156 (2), 366–376 (1987).

Stuiver et al., *J. Virology*, 65:379–386 (1990).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

CACTTAATTA AACGCCTACA TGGGGGTAGA GT        32

-continued ( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

CACTTAATTA AGGAAATATG ACTACGTCCG GCGT    34

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

GCCGCCTCAT CCGCTTTT    18

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

CCGGAATTCC ACCATGGCGA GTCGGGAAGA GG    32

COMPLEMENTARY ADENOVIRAL SYSTEMS AND CELL LINES

RELATED APPLICATIONS

This is a continuation-in-part application of copending PCT patent application PCT/U.S.95/07341, filed Jun. 7, 1995, which is a continuation-in-part of copending U.S. patent application Ser. No. 08/258,416, filed Jun. 10, 1994.

TECHNICAL FIELD OF THE INVENTION

The present invention relates to recombinant, multiply replication deficient adenoviral vectors having a spacer in at least one of the replication deficient adenoviral regions and to the therapeutic use of such vectors.

BACKGROUND OF THE INVENTION

During the winter and spring of 1952–1953, Rowe and his colleagues at the National Institutes of Health (NIH) obtained and placed in tissue culture adenoids that had been surgically removed from young children in the Washington, D.C. area (Rowe et al., *Proc. Soc. Exp. Biol. Med.,* 84, 570–573 (1953)). After periods of several weeks, many of the cultures began to show progressive degeneration characterized by destruction of epithelial cells. This cytopathic effect could be serially transmitted by filtered culture fluids to established tissue cultures of human cell lines. The cytopathic agent was called the "adenoid degenerating" u(Ad) agent. The name "adenovirus" eventually became common for these agents. The discovery of many prototype strains of adenovirus, some of which caused respiratory illnesses, followed these initial discoveries (Rowe et al., supra; Dingle et al., *Am. Rev. Respir. Dis.,* 97, 1–65 (1968); reviewed in Horwitz, "Adenoviridae and Their Replication," in *Virology* (Fields et al., eds., Raven Press Ltd., New York, N.Y., 2d ed., 1990), pp. 1679–1721).

Over 40 adenoviral subtypes have been isolated from humans and over 50 additional subtypes have been isolated from other mammals and birds (reviewed in Ishibashi et al., "Adenoviruses of animals," in *The Adenoviruses*, Ginsberg, ed., Plenum Press, New York, N.Y., pp. 497–562 (1984); Strauss, "Adenovirus infections in humans," in *The Adenoviruses*, Ginsberg, ed., Plenum Press, New York, N.Y., pp. 451–596 (1984)). All these subtypes belong to the family Adenoviridae, which is currently divided into two genera, namely Mastadenovirus and Aviadenovirus.

All adenoviruses are morphologically and structurally similar. In humans, however, adenoviruses have diverging immunological properties and, therefore, are divided into serotypes. Two human serotypes of adenovirus, namely Ad2 and Ad5, have been studied intensively. These studies have provided the majority of information about adenoviruses in general. The Ad2 and Ad5 genomes have been completely sequenced and sequences of selected regions of genomes from other serotypes are available as well. The overall organization of the adenoviral genome is conserved among serotypes, such that specific functions are similarly positioned.

In general, adenoviruses are nonenveloped, regular icosahedrons, of about 65 to 80 nanometers in diameter, consisting of an external capsid and an internal core. The capsid is composed of 20 triangular surfaces, or facets, and 12 vertices (Horne et al., *J. Mol. Biol.,* 1, 84–86 (1959)). The facets are comprised of hexons, and the vertices are comprised of pentons. A fiber projects from each of the vertices. In addition to the hexons, pentons, and fibers, there are eight minor structural polypeptides, the exact positions of the majority of which are unclear. One minor polypeptide component, namely polypeptide IX, binds at positions where it can stabilize hexon—hexon contacts at what is referred to as the "group-of-nine" center of each facet (Furcinitti et al., *EMBO,* 8, 3563–3570 (1989)). The minor polypeptides VI and VIII are believed to stabilize hexon-hexon contacts between adjacent facets. The minor polypeptide IIIA, which is known to be located in the regions of the vertices, has been suggested by Stewart et al. (*Cell,* 67, 145–154 (1991)) to link the capsid and the core.

The viral core contains a linear, double-stranded DNA molecule with inverted terminal repeats (ITRs), which have been noted to vary in length from 103 base pairs to 163 base pairs in different isolates (Garon et al., *Proc. Natl. Acad. Sci. USA,* 69, 2391–2394 (1972); Wolfson et al., *Proc. Natl. Acad. Sci. USA,* 69, 3054–3057 (1972); Arrand et al., *J. Mol. Biol.,* 128, 577–594 (1973); Steenberg et al., *Nucleic Acids Res.,* 4, 4371–4389 (1977); and Tooze, *DNA Tumor Viruses,* 2nd ed., Cold Spring Harbor, New York: Cold Spring Harbor Laboratory. pp. 943–1054 (1981)). The ITRs harbor origins of DNA replication (Garon et al., supra; Wolfson et al., supra; Arrand et al., supra; Steenberg et al., supra).

The viral DNA is associated with four polypeptides, namely V, VII, $\mu$, and terminal polypeptide (TP). The 55 kilodalton TP is covalently linked to the 5' ends of the DNA via a dCMP (Rekosh et al., *Cell,* 11, 283–295 (1977); Robinson et al., *Virology,* 56, 54–69 (1973)). The other three polypeptides are noncovalently bound to the DNA and fold it in such a way as to fit it into the small volume of the capsid. The DNA appears to be packaged into a structure similar to cellular nucleosomes as seen from nuclease digestion patterns (Corden et al., *Proc. Natl. Acad. Sci. USA,* 73, 401–404 (1976); Tate et al., *Nucleic Acids Res.,* 6, 2769–2785 (1979); Mirza et al., *Biochim. Biophys. Acta,* 696, 76–86 (1982)).

An adenovirus infects a cell by attachment of the fiber to a specific receptor on the cell membrane (Londberg-Holm et al., *J. Virol.,* 4, 323–338 (1969); Morgan et al., *J. Virol.,* 4, 777–796 (1969); Pastan et al., "Adenovirus entry into cells: some new observations on an old problem," in *Concepts in Viral Pathogenesis*, Notkins et al., eds., Springer-Verlag, New York, N.Y., pp. 141–146 (1987)). Then, the penton base binds to an adenoviral integrin receptor. The receptor-bound virus then migrates from the plasma membrane to clathrin-coated pits that form endocytic vesicles or receptosomes, where the pH drops to 5.5 (Pastan et al., *Concepts in Viral Pathogenesis*, Notkins and Oldstone, eds. Springer-Verlag, New York. pp. 141–146 (1987)). The drop in pH is believed to alter the surface configuration of the virus, resulting in receptosome rupture and release of virus into the cytoplasm of the cell. The viral DNA is partially uncoated, i.e., partially freed of associated proteins, in the cytoplasm while being transported to the nucleus.

When the virus reaches the nuclear pores, the viral DNA enters the nucleus, leaving most of the remaining protein behind in the cytoplasm (Philipson et al., *J. Virol.,* 2, 1064–1075 (1968)). However, the viral DNA is not completely protein-free in that at least a portion of the viral DNA is associated with at least four viral polypeptides, namely V, VII, TP and $\mu$, and is converted into a viral DNA-cell histone complex (Tate et al., *Nucleic Acids Res.,* 6, 2769–2785 (1979)).

The cycle from cell infection to production of viral particles lasts about one to two days and results in the production of up to about 10,000 infectious particles per cell (Green et al., *Virology*, 13, 169–176 (1961)). The infection process of adenovirus is divided into early (E) and late (L) phases, which are separated by viral DNA replication, although some events which take place during the early phase also take place during the late phase and vice versa. Further subdivisions have been made to fully describe the temporal expression of viral genes.

During the early phase, viral mRNA, which constitutes a minor proportion of the total RNA present in the cell, is synthesized from both strands of the adenoviral DNA present in the cell nucleus. At least five regions, designated E1, E2, E3, E4, and MLP-L1, are transcribed (Lewis et al., *Cell*, 7, 141–151 (1976); Sharp et al., *Virology*, 75, 442–456 (1976); Sharp, "Adenovirus transcription," in *The Adenoviruses*, Ginsberg, ed., Plenum Press, New York, N.Y., pp. 173–204 (1984)). Each region has at least one distinct promoter and is processed to generate multiple mRNA species.

The products of the early (E) regions (1) serve regulatory roles for the expression of other viral components, (2) are involved in the general shut-off of cellular DNA replication and protein synthesis, and (3) are required for viral DNA replication. The intricate series of events regulating early mRNA transcription begins with expression of certain immediate early regions, including E1A, L1, and the 13.5 kilodalton gene (reviewed in Sharp (1984), supra; Horwitz (1990), supra). Expression of the delayed early regions E1B, E2A, E2B, E3 and E4 is dependent on the E1A gene products. Three promoters, the E2 promoter at 72 map units (mu), the protein IX promoter, and the IVa promoter are enhanced by the onset of DNA replication but are not dependent on it (Wilson et al., *Virology*, 94, 175–184 (1979)). Their expression characterizes an intermediate phase of viral gene expression. The result of the cascade of early gene expression is the start of viral DNA replication.

Initiation of viral DNA replication appears to be essential for entry into the late phase. The late phase of viral infection is characterized by the production of large amounts of the viral structural polypeptides and the nonstructural proteins involved in capsid assembly. The major late promoter (MLP) becomes fully active and produces transcripts that originate at 16.5 mu and terminate near the end of the genome. Post-transcriptional processing of this long transcript gives rise to five families of late mRNA, designated respectively as L1 to L5 (Shaw et al., *Cell*, 22, 905–916 (1980)). The mechanisms that control the shift from the early to late phase and result in such a dramatic shift in transcriptional utilization are unclear. The requirement for DNA replication may be a cis-property of the DNA template, because late transcription does not occur from a superinfecting virus at a time when late transcription of the primary infecting virus is active (Thomas et al., *Cell*, 22, 523–533 (1980)).

Certain recombinant adenoviral vectors have been used in gene therapy. The use of a recombinant adenoviral vector to transfer one or more recombinant genes enables targeted delivery of the gene or genes to an organ, tissue, or cells in need of treatment, thereby overcoming the delivery problem encountered in most forms of somatic gene therapy. Furthermore, recombinant adenoviral vectors do not require host cell proliferation for expression of adenoviral proteins (Horwitz et al., in *Virology, Raven Press, New York*, 2, 1679–1721 (1990); and Berkner, *BioTechniques*, 6, 616 (1988)). Moreover, if the diseased organ in need of treatment is the lung, use of adenovirus as the vector of genetic information has the added advantage of adenovirus being normally trophic for the respiratory epithelium (Straus, in *Adenoviruses*, Plenum Press, New York, pp. 451–496 (1984)).

Other advantages of adenoviruses as potential vectors for human gene therapy are as follows: (i) recombination is rare; (ii) there are no known associations of human malignancies with adenoviral infections despite common human infection with adenoviruses; (iii) the adenoviral genome (which is linear, double-stranded DNA) currently can be manipulated to accommodate foreign genes ranging in size up to 7.0–7.5 kb in length; (iv) an adenoviral vector does not insert its DNA into the chromosome of a cell, so its effect is impermanent and unlikely to interfere with the cell's normal function; (v) the adenovirus can infect non-dividing or terminally differentiated cells, such as cells in the brain and lungs; and (vi) live adenovirus, having as an essential characteristic the ability to replicate, has been safely used as a human vaccine (Horwitz et al., supra; Berkner et al., *J. Virol.*, 61, 1213–1220 (1987); Straus supra; Chanock et al., *JAMA*, 195, 151 (1966); Haj-Ahmad et al., *J. Virol.*, 57, 267 (1986); and Ballay et al., *EMBO*, 4, 3861 (1985)).

Foreign genes have been inserted into two major regions of the adenoviral genome for use as expression vectors, namely the E1 and E3 regions, thus providing singly deficient adenovirus and vectors derived therefrom. Insertion into the E1 region results in defective progeny that require either growth in complementary cells or the presence of an intact helper virus, either of which serves to replace the function of the impaired or absent E1 region (Berkner et al., supra; Davidson et al., *J. Virol.*, 61, 1226–1239 (1987); and Mansour et al., *Mol. Cell Biol.*, 6, 2684–2694 (1986)). This region of the genome has been used most frequently for expression of foreign genes.

The genes inserted into the E1 region have been placed under the control of various promoters and most produce large amounts of the foreign gene product, dependent on the expression cassette. These adenoviral vectors, however, will not grow in noncomplementing cell lines. Currently, there are only a few cell lines that exist that will complement for essential functions missing from a singly deficient adenovirus. Examples of such cell lines include HEK-293 (Graham et al., *Cold Spring Harbor Symp. Quant. Biol.*, 39, 637–650 (1975)), W162 (Weinberg et al., *Proc. Natl. Acad. Sci. USA*, 80, 5383–5386 (1983)), and gMDBP (Klessig et al., *Mol. Cell. Biol.*, 4, 1354–1362 (1984); Brough et al., *Virology*, 190, 624–634 (1992)).

In comparison, the E3 region is nonessential for virus growth in tissue culture (i.e., viral production), and replacement of this region with a foreign gene expression cassette leads to a virus that can productively grow in a noncomplementing cell line. For example, the insertion and expression of the hepatitis B surface antigen in the E3 region with subsequent inoculation and formation of antibodies in the hamster has been reported (Morin et al., *Proc. Natl. Acad. Sci. USA*, 84, 4626–4630 (1987)).

One problem associated with use of singly deficient adenoviral vectors is they limit the amount of usable space within the adenoviral genome for insertion and expression of a foreign gene. Moreover, due to similarities, or overlap, in the viral sequences contained within the singly deficient adenoviral vectors and the complementing cell lines that currently exist, recombination events can take place and create replication competent viruses within a vector stock so propagated. This event can render a stock of vector unusable for gene therapy purposes.

Multiply replication deficient vectors (i.e., vectors deficient in at least two regions required for viral production) have been derived in an effort to overcome this problem (PCT patent application WO 94/28152 (Imler et al.)). Such vectors having at least one of the deletions in the E2 or E4 regions, however, exhibit reduced fiber expression and reduced viral growth in complementing cell lines. The E4 region in particular is suspected to have a role in viral DNA replication, late mRNA synthesis, host protein synthesis shut off and viral assembly. Recently, in an attempt to correct the reduced viral growth of vectors deficient in E4 regions in complementing cell lines, adenoviral vectors were designed having E4 deletions, and which retained essential open reading frames of the E4 region, specifically ORF6 or ORF 3 (PCT patent application WO 94/12649 (Gregory et al.)).

Whereas either open reading frame 3 or 6 is capable of supplying E4 functions required for virus propagation in vitro, the ORF 3 product does so with reduced efficiency (Armentano et al., *Human Gene Therapy*, 6, 1343–1353 (1995)). Moreover, several properties associated with the ORFs that might function in vivo have been described (see, e.g., Armentano et al., supra). For instance, the product of ORF 6/7 is involved in activation of the E2A promoter through complex formation with, and stimulation of, the cellular transcription factor E2f. Similarly, both ORF3 and ORF6 are involved in the regulation of intron inclusion/exclusion in splicing of the major late tripatite leader. However, even ORF 6 is not able to impart wild-type viral production to an adenoviral E4 deletion mutant. Specifically, an adenoviral E1⁻ E4⁻ deletion mutant containing ORF 6 exhibited a 10-fold reduction in fiber synthesis, delayed virus replication and slower plaque formation in vitro, and reduced and delayed viral replication in vivo, as compared to an adenovirus not having the E4 deletion (Armentano et al., supra).

Accordingly, it is an object of the present invention to provide multiply replication deficient adenoviral vectors which can accommodate the insertion and expression of relatively large pieces of foreign DNA while being capable of satisfactory replication in vitro, i.e., viral production. It is also an object of the present invention to provide recombinants of such multiply replication deficient adenoviral vectors and therapeutic methods, particularly relating to gene therapy, vaccination, and the like, involving the use of such recombinants. These and other objects and advantages of the present invention, as well as additional inventive features, will be apparent from the following detailed description.

BRIEF SUMMARY OF THE INVENTION

The present invention provides multiply replication deficient adenoviral vectors and complementing cell lines. The multiply replication deficient adenoviral vectors have a spacer in at least one of the replication deficient adenoviral regions. These multiply replication deficient adenoviral vectors can accommodate the insertion and expression of larger fragments of foreign DNA than is possible with singly replication deficient adenoviral vectors, yet provide similar fiber expression and viral growth as found in singly replication deficient adenoviral vectors. The present invention also provides recombinant multiply replication deficient adenoviral vectors and therapeutic methods, for example, relating to gene therapy, vaccination, and the like, involving the use of such recombinants.

DETAILED DESCRIPTION OF THE INVENTION

Figure 1:
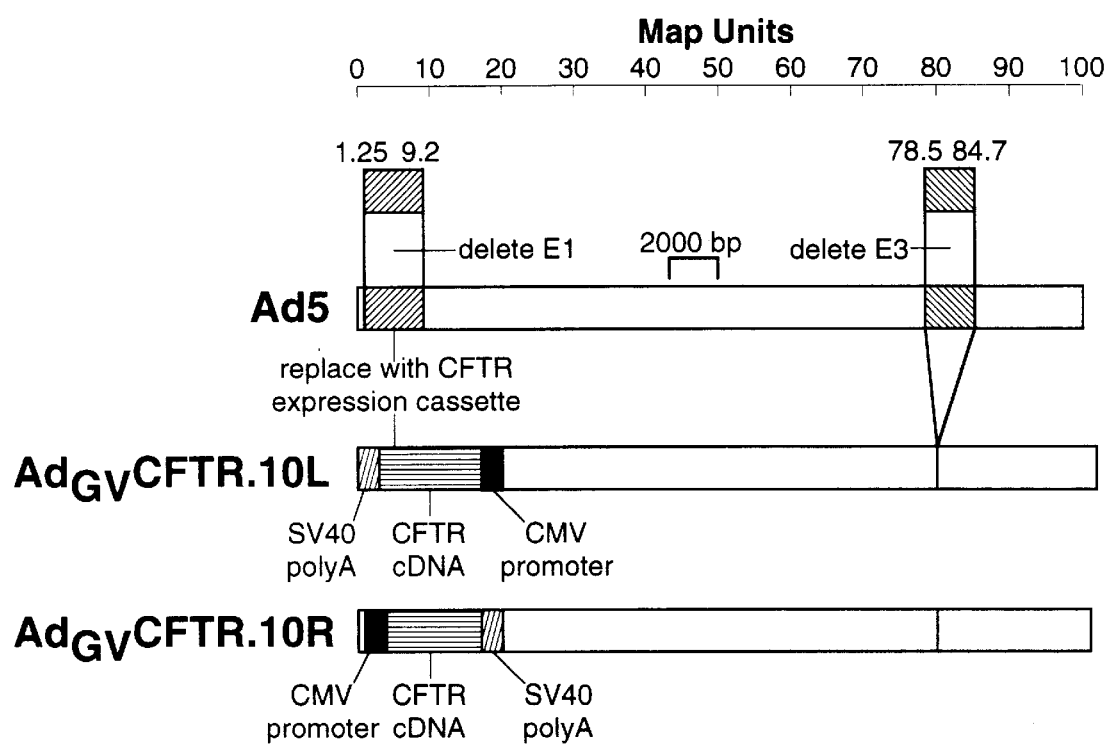
FIG. 1 is a set of schematic diagrams of the $Ad_{GV}CFTR.10L$ and $Ad_{GV}CFTR.10R$ viral vectors.

The present invention provides, among other things, multiply replication deficient adenoviral vectors for gene cloning and expression. The multiply replication deficient adenoviral vectors of the present invention differ from currently available singly replication deficient adenoviral vectors in being deficient in at least two regions of the adenoviral genome, especially two such regions required for viral production, thereby allowing such vectors to accept and express larger pieces of foreign DNA. The term "foreign DNA" or "passenger gene" is used herein to refer to any sequence of DNA inserted into a vector (i.e., a transfer vector) of the present invention that is foreign to the adenoviral genome. Such foreign DNA may constitute genes, portions of genes, or any other DNA sequence, including but not limited to sequences that encode RNA, anti-sense RNA, and/or polypeptides. The multiply replication deficient adenoviral vectors of the present invention also differ from recently discovered multiply replication deficient adenoviral vectors in being able to achieve fiber expression and viral growth in a complementing cell line similar to a singly replication deficient vector by virtue of the presence of a spacer in at least one of the deficient adenoviral regions which may cause a transcriptional blockade thereby preventing transcriptional read-through.

A region of the adenoviral genome comprises one or more genes. Such genes encode gene products that mediate, facilitate, cause, or are the various components or activities of the adenovirus, such as attachment, penetration, uncoating, replication, core protein, hexon, fiber, hexon associated protein, and the like. One effect of a deficient region can be an inability of the adenovirus to propagate, for example, which may involve any or all of the aforementioned components or activities. The aforementioned components or activities are referred to herein as gene functions.

A deficiency in a gene or gene function, i.e., a deficient gene, gene region, or region, as used herein is defined as a deletion of genetic material of the viral genome, which serves to impair or obliterate the function of the gene whose DNA sequence was deleted in whole or in part and to provide room in or capacity of the viral genome for the insertion of DNA that is foreign to the viral genome. Such deficiencies may be in genes that are essential or unessential for propagation of the adenoviral vector in tissue culture in a noncomplementing cellular host; preferably, at least one, more preferably, at least two, of the deficient genes of the inventive viral vectors are deficient for a gene that is essential for viral propagation.

Any subtype, mixture of subtypes, or chimeric adenovirus can be used as the source of DNA for generation of the multiply deficient adenoviral vectors. However, given that the Ad5 genome has been completely sequenced, the present invention is described with respect to the Ad5 serotype.

The adenoviral vector of the present invention is desirably multiply replication deficient, i.e., it is deficient in at least two regions required for viral production (i.e., viral replication in vitro). Such regions include early region 1 (E1), early region 2A (E2A), early region 2B (E2B), early region 4 (E4), late region 1 (L1), late region 2 (L2), late region 3 (L3), late region 4 (L4), and late region 5 (L5). Even though the E1 region can be considered as consisting of early region 1A (E1A) and early region 1B (E1B), a deficiency in either or both of the E1A and/or E1B regions is considered as a single deficiency in the context of the present invention. In addition, such a vector can be deficient in one or more regions which are not required for viral production, e.g., the vectors can be additionally deficient in early region 3 (E3).

The present inventive adenoviral vector will be desirably deficient in the E4 region and one or more additional regions required for viral production (especially other early regions required for viral production), preferably with the entire E4 region having been deleted from the adenoviral vector, except possibly for the polyadenylation sequence between the retained L5 fiber region and the right-side ITR. More preferably, the deficient additional region required for viral production will be the E1 and/or E2A region, with even more preferably the E3 region also being removed. Thus, preferred embodiments of the present inventive adenoviral vector include E1⁻ E2A⁻, E1⁻ E2A⁻ E4⁻, E1⁻ E4⁻, and E2A⁻ E4⁻ adenoviral vectors, which can also be E3⁻. Most preferably, all of the early regions are removed from the adenoviral vector (with or without the removal of the late regions, preferably while at least retaining the L5 fiber region), except possibly for the aforesaid E4 polyadenylation sequence between the retained L5 fiber region and the right-side ITR.

The present inventive adenoviral vector includes a spacer to provide viral growth in a complementing cell line similar to that achieved by singly replication deficient adenoviral vectors, particularly a singly replication deficient E1 deficient adenoviral vector. In the preferred E4⁻ adenoviral vector of the present invention wherein the L5 fiber region is retained, the spacer is desirably located between the L5 fiber region and the right-side ITR. More preferably in such an adenoviral vector, the E4 polyadenylation sequence alone or, most preferably, in combination with another sequence exists between the L5 fiber region and the right-side ITR, so as to sufficiently separate the retained L5 fiber region from the right-side ITR, such that viral production of such a vector approaches that of a singly replication deficient adenoviral vector, particularly a singly replication deficient E1 deficient adenoviral vector.

In the absence of a spacer, production of fiber protein and/or viral growth of the multiply replication deficient adenoviral vector is reduced by comparison to that of a singly replication deficient adenoviral vector. However, inclusion of the spacer in at least one of the deficient adenoviral regions, preferably the E4 region, counteracts this defect in growth and fiber expression.

The function of the replication deficient region is provided by a complementing cell line. As a result, the spacer does not need to provide the deficient function and can be any sequence, limited only by the size of the insert that the vector will accommodate. The spacer alone can function to repair the growth defect and decreased fiber expression found in multiply replication deficient adenoviral vectors. The spacer can be of any suitable size, desirably at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs.

The spacer can contain any sequence or sequences which are of the desired length. The spacer sequence can be coding or non-coding and native or non-native with respect to the adenoviral genome, but does not restore the replication function to the deficient region. The spacer can also contain a promoter-variable expression cassette. More preferably, the spacer comprises an additional polyadenylation sequence and/or a passenger gene. Preferably, in the case of a spacer inserted into a region deficient for E4, both the E4 polyadenylation sequence and the E4 promoter of the adenoviral genome or any other (cellular or viral) promoter remain in the vector. The spacer is located between the E4 polyadenylation site and the E4 promoter, or, if the E4 promotor is not present in the vector, the spacer is proximal to the right-side ITR.

The spacer can comprise any suitable polyadenylation sequence. Examples of suitable polyadenylation sequences include synthetic optimized sequences, BGH (Bovine Growth Hormone), polyoma virus, TK (Thymidine Kinase), EBV (Epstein Barr Virus) and the papillomaviruses, including human papillomaviruses and BPV (Bovine Papilloma Virus). Preferably, particularly in the E4 deficient region, the spacer includes an SV40 polyadenylation sequence. The SV40 polyadenylation sequence allows for higher virus production levels of multiply replication deficient adenoviral vectors.

Although a passenger gene is typically inserted into the E1 deficient region of an adenoviral genome, a passenger gene can also function as the spacer in the E4 deficient region of the adenoviral genome. The passenger gene is limited only by the size of the fragment the vector can accommodate and can be any suitable gene. Examples of suitable passenger genes include marker gene sequences such as pGUS, secretory alkaline phosphatase, luciferase, B-galactosidase, and human anti-trypsin; therapeutic genes of interest such as the cystic fibrosis transmembrane regulator gene (CFTR); and potential immune modifiers such as B3-19K, E3-14.7, ICP47, fas ligand gene, and CTLA4 gene.

Preferably, a multiply replication deficient adenoviral vector of the present invention that is deficient in the E2A region further comprises a portion of the E2A region of the adenoviral genome in the E2A deficient region which is less than about 230 base pairs in length. Generally, the E2A region of the adenovirus codes for DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and posttranscriptional levels, is responsible for efficient nuclear localization of the protein, and may also play a role in enhancement of its own expression. Deletions in the Nt domain between amino acids 2 to 38 have indicated that this region is important for DBP function. (Brough et al., Virology, 196, 269–281 (1993)). While deletions in the E2A region coding for the Ct region of the DBP have no effect on viral production, deletions in the E2A region which code for amino acids 2 to 38 of the Nt domain of the DBP impair viral production. Therefore, it is preferable that any multiply replication deficient adenoviral vector contain this portion of the E2A region of the adenoviral genome.

In particular, for example, the desired portion of the E2A region to be retained is that portion of the E2A region of the adenoviral genome which is defined by the 5' end of the E2A region, specifically, positions Ad5(23816) to Ad5(24032) of the E2A region of the adenoviral genome of serotype Ad5, are required to render the vector replication competent in a complementing cell line. This portion of the adenoviral genome must be included in the adenoviral vector because it is not complemented in the current E2A cell lines, and in its absence the requisite levels of viral production and fiber expression cannot be obtained in complementing cell lines.

Any one of the deleted regions can be replaced with a promoter-variable expression cassette to produce a foreign gene product, that is foreign with respect to adenovirus. The insertion of a foreign gene into the E2A region, for example, may be facilitated by the introduction of a unique restriction site, such that the foreign gene product may be expressed from the E2A promoter.

The present invention is not limited to adenoviral vectors that are deficient in gene functions only in the early region of the genome. Also included are adenoviral vectors that are deficient in the late region of the genome, adenoviral vectors that are deficient in the early and late regions of the genome, as well as vectors in which essentially the entire genome has been removed, in which case it is preferred that at least either the viral inverted terminal repeats and some of the promoters or the viral inverted terminal repeats and a packaging signal are left intact. One of ordinary skill in the art will appreciate that the larger the region of the adenoviral genome that is removed, the larger the piece of exogenous DNA that can be inserted into the genome. For example, given that the adenoviral genome is 36 kb, by leaving the viral inverted terminal repeats and some of the promoters intact, the capacity of the adenovirus is approximately 35 kb. Alternatively, one could generate a multiply deficient adenoviral vector that contains only the ITR and a packaging signal. This could then effectively allow for expression of 37–38 kb of foreign DNA from this vector. Of course, the inclusion of a spacer sequence in any or all of the deficient adenoviral regions will decrease the capacity of the adenoviral vector in size corresponding with the size of the spacer sequence.

In general, virus vector construction relies on the high level of recombination between fragments of adenoviral DNA in the cell. Two or three fragments of adenoviral DNA, containing regions of similarity (or overlap) between fragments and constituting the entire length of the genome, are transfected into a cell. The host cell's recombination machinery constructs a full-length viral vector genome by recombining the aforementioned fragments. Other suitable procedures for constructing viruses containing alterations in various single regions have been previously described (Berkner et al., Nucleic Acids Res., 12, 925–941 (1984); Berkner et al., Nucleic Acids Res., 11, 6003–6020 (1983); Brough et al., Virol., 190, 624–634 (1992)) and can be used to construct multiply deficient viruses; yet other suitable procedures include in vitro recombination and ligation, for example.

The first step in virus vector construction is to construct a deletion or modification (such as adding a spacer to a deleted region) of a particular region of the adenoviral genome in a plasmid cassette using standard molecular biological techniques. After extensive analysis, this altered DNA (containing the deletion or modification) is then moved into a much larger plasmid that contains up to one half of the adenovirus genome. The next step is to transfect the plasmid DNA (containing the deletion or modification) and a large piece of the adenovirus genome into a recipient cell. Together these two pieces of DNA encompass all of the adenovirus genome plus a region of similarity. Within this region of similarity a recombination event will take place to generate a recombed viral genome that includes the deletion or modification. In the case of multiply replication deficient vectors, the recipient cell will provide not only the recombination functions but also all missing viral functions not contained within the transfected viral genome, thus complementing any deficiencies of the recombined viral genome. The multiply replication deficient vector can be further modified by alteration of the ITR and/or packaging signal, for example, such that the multiply replication deficient vector only functions or grows in a complementing cell line.

In addition, the present invention also provides complementing cell lines for propagation or growth of the present inventive multiply deficient adenoviral vectors. The preferred cell lines of the present invention are characterized in complementing for at least one gene function of the gene functions comprising the E1, E2, and E4 regions of the adenoviral genome. Other cell lines include those that complement adenoviral vectors that are deficient in at least one gene function from the gene functions comprising the late regions, those that complement for a combination of early and late gene functions, and those that complement for all adenoviral functions. One of ordinary skill in the art will appreciate that the cell line of choice is one that specifically complements for those functions that are missing from the recombinant multiply deficient adenoviral vector of interest and that are generated using standard molecular biological techniques. The cell lines are further characterized in containing the complementing genes in a nonoverlapping fashion, which minimizes, practically eliminating, the possibility of the vector genome recombining with the cellular DNA. Accordingly, replication-competent adenoviruses are eliminated from the vector stocks, which are, therefore, suitable for certain therapeutic purposes, especially gene therapy purposes. This also eliminates the replication of the adenoviruses in noncomplementing cells.

The complementing cell line must be one that is capable of expressing the products of the two or more deficient adenoviral gene functions at the appropriate level for those products in order to generate a high titer stock of recombinant adenoviral vector. For example, it is necessary to express the E2A product, DBP, at stoichiometric levels, i.e., relatively high levels, for adenoviral DNA replication, but the E2B product, Ad pol, is necessary at only catalytic levels, i.e., relatively low levels, for adenoviral DNA replication. Not only must the level of the product be appropriate, the temporal expression of the product must be consistent with that seen in normal viral infection of a cell to assure a high titer stock of recombinant adenoviral vector. For example, the components necessary for viral DNA replication must be expressed before those necessary for virion assembly. In order to avoid cellular toxicity, which often accompanies high levels of expression of the viral products, and to regulate the temporal expression of the products, inducible promoter systems are used. For example, the sheep metallothionine inducible promoter system can be used to express the complete E4 region, the open reading frame 6 of the E4 region, and the E2A region. Other examples of suitable inducible promoter systems include, but are not limited to, the bacterial lac operon, the tetracycline operon, the T7 polymerase system, and combinations and chimeric constructs of eukaryotic and prokaryotic transcription factors, repressors and other components. Where the viral product to be expressed is highly toxic, it is desirable to use a bipartite inducible system, wherein the inducer is carried in a viral vector and the inducible product is carried within the chromatin of the complementing cell line. Repressible/inducible expression systems, such as the tetracycline expression system and lac expression system also may be used.

DNA that enters a small proportion of transfected cells can become stably maintained in an even smaller fraction. Isolation of a cell line that expresses one or more transfected genes is achieved by introduction into the same cell of a second gene (marker gene) that, for example, confers resistance to an antibiotic, drug or other compound. This selection is based on the fact that, in the presence of the antibiotic, drug, or other compound, the cell without the transferred gene dies, while the cell containing the transferred gene survives. The surviving cells are then clonally isolated and expanded as individual cell lines. Within these cell lines are those that express both the marker gene and the gene or genes of interest. Propagation of the cells is dependent on the parental cell line and the method of selection. Transfection of the cell is also dependent on cell type. The most common techniques used for transfection are calcium phosphate precipitation, liposome, or DEAE dextran mediated DNA transfer.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of a given gene and can be constructed by conventional synthetic or site-specific mutagenesis procedures. Synthetic DNA methods can be carried out in substantial accordance with the procedures of Itakura et al., *Science,* 198, 1056 (1977) and Crea et al., *Proc. Natl. Acad. Sci. USA,* 75, 5765 (1978). Site-specific mutagenesis procedures are described in Maniatis et al., *Molecular Cloning: A Laboratory Manual,* Cold Spring Harbor, N.Y. (2d ed. 1989). Therefore, the present invention is in no way limited to the DNA sequences and plasmids specifically exemplified herein. Exemplified vectors are for gene therapy of cystic fibrosis and, therefore, contain and express the cystic fibrosis transmembrane regulator (CFTR) gene, however the vectors described are easily convertible to treat other diseases including, but not limited to, other chronic lung diseases, such as emphysema, asthma, adult respiratory distress syndrome, and chronic bronchitis, as well as cancer, coronary heart disease, and other afflictions suitably treated or prevented by gene therapy, vaccination, and the like. Accordingly, any gene or DNA sequence can be inserted into a multiply deficient adenoviral vector. The choice of gene or DNA sequence is one that achieves a therapeutic and/or prophylactic effect, for example, in the context of gene therapy, vaccination, and the like.

One skilled in the art will appreciate that suitable methods of administering a multiply deficient adenoviral vector of the present invention to an animal for therapeutic or prophylactic purposes, e.g., gene therapy, vaccination, and the like (see, for example, Rosenfeld et al., *Science*, 252, 431–434 (1991), Jaffe et al., *Clin. Res.*, 39(2), 302A (1991), Rosenfeld et al., *Clin. Res.*, 39(2), 311A (1991), Berkner, *BioTechniques*, 6, 616–629 (1988)), are available, and, although more than one route can be used to administer the vector, a particular route can provide a more immediate and more effective reaction than another route. Pharmaceutically acceptable excipients are also well-known to those who are skilled in the art, and are readily available. The choice of excipient will be determined in part by the particular method used to administer the composition. Accordingly, there is a wide variety of suitable formulations of the pharmaceutical composition of the present invention. The following formulations and methods are merely exemplary and are in no way limiting. However, oral, injectable and aerosol formulations are preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The vectors of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the vectors employed in the present invention may be made into suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene or other sequence of interest, the composition employed, the method of administration, and the particular site and organism being treated. The dose should be sufficient to effect a desirable response, e.g., therapeutic or prophylactic response, within a desirable time frame.

The multiply deficient adenoviral vectors and complementing cell lines of the present invention also have utility in vitro. For example, they can be used to study adenoviral gene function and assembly, or expression of foreign DNA in a suitable target cell. One of ordinary skill can identify a suitable target cell by selecting one that can be transfected by the inventive adenoviral vector and/or infected by adenoviral particles, resulting in expression of the thereby inserted adenoviral DNA complement. Preferably, a suitable target cell is selected that has receptors for attachment and penetration of adenovirus into a cell. Such cells include, but are not limited to, those originally isolated from any mammal. Once the suitable target cell has been selected, the target cell is contacted with a foreign DNA-containing recombinant multiply deficient adenoviral vector or adenoviral particle of the present invention, thereby effecting transfection or infection, respectively. Expression, toxicity, and other parameters relating to the insertion and activity of the foreign DNA in the target cell is then measured using conventional methods well known in the art. In so doing, researchers can learn and elucidate the phenomenology concerning adenoviral infection as well as the efficacy and effect of expression of various sequences of foreign DNA introduced by the inventive vector in various cell types that are explanted from various organisms and studied in tissue culture.

Moreover, cells explanted or removed from a patient having a disease that is suitably treated by gene therapy in the context of the present invention usefully are manipulated in vitro. For example, cells cultured in vitro from such an individual are placed in contact with an adenoviral vector of the present invention under suitable conditions to effect transfection, which are readily determined by one of ordinary skill in the art, where the vector includes a suitable foreign DNA. Such contact suitably results in transfection of the vector into the cultured cells, where the transfected cells are selected for using a suitable marker and selective culturing conditions. In so doing, using standard methods to test for vitality of the cells and thus measure toxicity and to test for presence of gene products of the foreign gene or genes of the vector of interest and thus measure expression, the cells of the individual are tested for compatibility with, expression in, and toxicity of the foreign gene-containing vector of interest, thereby providing information as to the appropriateness and efficacy of treatment of the individual with the vector/foreign DNA system so tested. Such explanted and transfected cells, in addition to serving to test the potential efficacy/toxicity of a given gene therapy regime, can be also returned to an in vivo position within the body of the individual. Such cells so returned to the individual may be returned unaltered and unadorned except for the in vitro transfection thereof, or encased by or embedded in a matrix that keeps them separate from other tissues and cells of the individual's body. Such a matrix may be any suitable biocompatible material, including collagen, cellulose, and the like. Of course, alternatively or in addition, once having observed a positive response to the in vitro test, the transfection can be implemented in situ by administration means as detailed hereinabove.

The following examples further illustrate the present invention and, of course, should not be construed as in any way limiting its scope. Enzymes referred to in the examples are available, unless otherwise indicated, from Bethesda Research Laboratories (BRL), Gaithersburg, Md. 20877, New England Biolabs Inc. (NEB), Beverly, Mass. 01915, or Boehringer Mannheim Biochemicals (BMB), 7941 Castleway Drive, Indianapolis, Ind. 46250, and are used in substantial accordance with the manufacturer's recommendations. Many of the techniques employed herein are well known to those in the art. Molecular biology techniques are described in detail in suitable laboratory manuals, such as Maniatis et al., *Molecular Cloning: A Laboratory Manual*, Cold Spring Harbor, N.Y. (2d ed. 1989), and *Current Protocols in Molecular Biology* (Ausubel et al., eds. (1987)). One of ordinary skill in the art will recognize that alternate procedures can be substituted for various procedures presented below. Although the examples and figures relate to $Ad_{GV}.10$, $Ad_{GV}.11$, $Ad_{GV}.11S$, $Ad_{GV}.12$, and $Ad_{GV}.13$ which contain, for instance, a reporter gene or a therapeutic gene such as the cystic fibrosis transmembrane regulator gene (CFTR), to comprise, for example, $Ad_{GV}$CFTR.10, $Ad_{GV}$CFTR.11, $Ad_{GV}$GUS.11S, $Ad_{GV}$CFTR.12, and $Ad_{GV}$CFTR.13, these vectors are not limited to expression of the CFTR gene and can be used to express other genes and DNA sequences. For example, therefore, the present invention encompasses such vectors comprising any suitable DNA sequence, which may be a foreign gene, a fragment thereof, or any other DNA sequence. Such a suitable DNA sequence may have use in gene therapy to treat a disease that is suitably treated by gene therapy. Alternatively, a suitable DNA sequence may also have a prophylactic use, such as when the DNA sequence is capable of being expressed in a mammal resulting in, for example, a polypeptide capable of eliciting an immune response to the polypeptide, as used in vaccination. Yet another alternative use of a suitable DNA sequence capable of being expressed in a mammal is to provide any other suitable therapeutic and/or prophylactic agent, such as an antisense molecule, particularly an antisense molecule selected from the group consisting of mRNA and a synthetic oligonucleotide.

EXAMPLE 1

This example describes the generation of one embodiment involving $Ad_{GV}.10$, namely $Ad_{GV}$CFTR.10, which is deficient in the E1 and E3 regions.

$Ad_{GV}$CFTR.10 expresses the CFTR gene from the cytomegalovirus (CMV) early promoter. Two generations of this vector have been constructed and are designated $Ad_{GV}$CFTR.10L and $Ad_{GV}$CFTR.10R, dependent on the direction in which the CFTR expression cassette is placed in the E1 region in relation to the vector genome as shown in FIG. 1, which is a set of schematic diagrams of $Ad_{GV}$CFTR.10L and $Ad_{GV}$CFTR.10R.

The CFTR expression cassette was constructed as follows. pRK5 (Genentech Inc., South San Francisco, Calif.) was digested with KpnI (New England Biolabs (NEB), Beverly, Mass.), blunt-ended with Mung Bean nuclease (NEB), and an Xho I linker (NEB) was ligated in place of the Kpn I site. The resulting vector was named pRK5-Xho I. pRK5-Xho I was then digested with Sma I (NEB) and Hin dIII (NEB) and blunt-ended with Mung bean nuclease. A plasmid containing the CFTR gene, pBQ4.7 (Dr. Lap-Chee Tsui, Hospital for Sick Children, Toronto, Canada), was digested with Ava I (NEB) and Sac I (NEB) and blunt-ended with Mung bean nuclease. These two fragments were isolated and ligated together to produce pRK5-CFTR1, the CFTR expression cassette.

pRK5-CFTR1 was digested with Spe I (NEB) and Xho I and blunt-ended with Klenow (NEB). pAd60.454 (Dr. L. E. Babiss, The Rockefeller University, New York, N.Y.), which contains Ad5 sequences from 1–454/3325–5788, was digested with Bg 1 II (NEB) and blunt-ended with Klenow. These two fragments were purified from vector sequences by low-melt agarose technique (Maniatis et al., *Molecular Cloning: a laboratory manual*, Cold Spring Harbor Laboratory, Cold Spring Harbor, N.Y. (2nd ed. 1989)) and ligated together to produce the left arm plasmids pGVCFTR.10L and pGVCFTR.10R.

The left arm plasmid from pGVCFTR.10L or pGVCFTR.10R was digested with Nhe I (NEB). The right arm of the virus was produced by digesting Ad5dl324 (Dr. Thomas E. Shenk, Princeton University, Princeton, N.J.) with Cla I (NEB). The two fragments, a small 918 bp fragment and a large approximately 32,800 bp fragment, were separated by sucrose gradient centrifugation (Maniatis et al., supra). The large fragment was mixed with the left arm plasmid fragments and transfected into 293 cells by standard calcium phosphate protocol (Graham et al., *Virology*, 52, 456 (1973)). The resulting recombinant viruses were plaque-purified on 293 cells, and viral stocks were established using standard virology techniques (e.g., Berkner et al., (1983) and (1984), supra).

EXAMPLE 2

This example describes the generation of one embodiment of $Ad_{GV}.11$, i.e., $Ad_{GV}$CFTR.11, which is deficient in the E1, E3, and E4 regions.

$Ad_{GV}.11$ is characterized by complete elimination of the E4 region. This large deletion allows for insertion of up to about 10 kb of exogenous DNA. More importantly, another region of the genome is accessible for introduction of foreign DNA expression cassettes using the $Ad_{GV}$CFTR.11 vectors. This deletion enables the incorporation of larger expression cassettes for other products. For example, soluble receptors, i.e., TNF or IL-6 without a transmembrane domain so that they are now not attached to the membrane, and antisense molecules, e.g., those directed against cell cycle regulating products, such as cdc2, cdk kinases, cyclins, i.e., cyclin E or cyclin D, and transcription factors, i.e., E2F or c-myc, to eliminate inflammation and immune responses.

$Ad_{GV}$CFTR.11 was constructed by means of a single in vivo recombination between 1–27082, i.e., the left arm, of $Ad_{GV}$CFTR.10 and a plasmid (pGV11A, pGV11B, pGV11C, or pGV11D; described in detail below) containing 21562–35935, i.e., the right arm, of Ad5 linearized with Bam HI (NEB) and Sal I (NEB) and into which the various E3 and E4 alterations as described below were introduced.

The left arm from $Ad_{GV}$ CFTR.10 was isolated on a concave 10–40% sucrose gradient, wherein ¼th of the total solution was 40%, after intact $Ad_{GV}$CFTR.10 was digested with Spe I (NEB) and Srf I (Stratagene, La Jolla, Calif.) to yield the 1–27082 bp fragment.

The right arm was obtained by Bam HI-Sal I digestion of a modified pGEM vector (pGBS). pGBS was generated as follows. pGemI (Promega, Madison, Wis.) was digested with Eco RI and blunt-ended with Klenow, and a Sal I linker was ligated into the vector. The resulting DNA was then digested with Sal I and religated, thereby replacing the Eco RI site with a Sal I site and deleting the sequence between the two Sal I sites, to generate pGEMH/P/S, which was digested with Hin dIII and blunt-ended with Klenow, and a Bam HI linker was ligated into the vector to generate pGEMS/B. pGEMS/B was digested with Bam HI and Sal I and ligated with an ~14 kb Bam HI-Sal I fragment (21562–35935 from Ad5) from a pBR plasmid called p50-100 (Dr. Paul Freimuth, Columbia University, N.Y.) to generate PGBS.

pGBSΔE3 is altered to produce a right arm plasmid in which the entire E4 region is deleted. The resulting plasmid in which the entire E3 and E4 regions are deleted is named pGV11(0). This is done by introducing a Pac I restriction site at the Afl III site at 32811 and the Bsg I site at 35640. Deletion of the Pac I fragment between these two sites effectively eliminates all of the E4 sequences including the E4 TATA element within the E4 promoter and the E4 poly A site.

Three different versions of the right arm plasmid were constructed in order to introduce into the adenoviral vector two Ad E3 gene products having anti-immunity and anti-inflammatory properties. The large E3 deletion in pGBSΔE30RF6, designated pGV11(0) (Example 7), was essentially replaced with three different versions of an expression cassette containing the Rous sarcoma virus-long terminal repeat (RSV-LTR) promoter driving expression of a bicistronic mRNA containing at the 5' end the Ad2 E3 19 kDa anti-immunity gene product and at the 3' end the Ad5 E3 14.7 Kda anti-inflammatory gene product. One additional virus was constructed by deleting the 19 kDa cDNA fragment by Bst BI (NEB) fragment deletion. This virus, designated $Ad_{GV}$CFTR.11(D), contains the RSV-LTR promoter driving expression of a monocistronic mRNA containing only the E3 14.7 kDa anti-inflammatory gene product.

The Spe I (27082) - Nde I (31089) fragment from pGBSΔE3 (Example 4) was subcloned into pUC 19 by first cloning the Eco RI (27331) - Nde I (31089) fragment into identical sites in the PUC 19 polylinker. A Hin dIII (26328) - Eco RI (27331) fragment generated from pGBS was then cloned into the Eco RI site of this clone to generate pHNΔE3. Using appropriate primers, a PCR fragment with flanking Xba I sites was generated containing the RSV-LTR promoter, the Ad2 E3 19 kDa gene product, and the Ad5 E3 14.7 kDa gene product. The amplified fragment was digested with Xba I and subcloned into pUC 19 to generate pXA. After analysis of the Xba I fragment, the fragment was ligated into pHNΔE3 to generate pHNRA.

Using appropriate primers, two PCR fragments with flanking Bst BI sites were generated that encode internal ribosomal entry sites (IRES), which are known to enhance the translation of mRNAs that contain them (Jobling et al., Nature, 325, 622–625 (1987); Jang et al., Genes and Development, 4, 1560–1572 (1990)). One fragment (version B) contains a 34 bp IRES from the untranslated leader of the coat protein mRNA of alfalfa mosaic virus (AMV RNA 4 leader) (Jobling et al., supra). The other fragment (version C) contains a 570 bp IRES from the 5' nontranslated region of encephalomyocarditis virus (EMCV) mRNA (Jang et al., supra). Each Bst BI fragment from version B or C was cloned in place of the Bst BI fragment in pXA. The resulting plasmids, named pXB and pXC, respectively, were moved into pHNΔE3 to generate pHNRB and pHNRC, respectively, after sequence analysis of the Xba I fragments.

The Spe I (27082) - Nde I (31089) fragment from pGBSΔE30RF6 was replaced with the Spe I - Nde I fragments from pHNRA, pHNRB, pHNRC and pHNRD to generate pGV11A, pGV11B, pGV11C and pGV11D, respectively.

The pGVx plasmid DNA was linearized with Bam HI and Sal I and mixed with the purified left arm DNA fragment in varying concentrations to give about 20 μg total DNA, using salmon sperm or calf thymus DNA (Life Technologies, Gaithersburg, Md.) to bring the amount of DNA to about 20 μg as needed. The mixed fragments were then transfected into 293 cells using standard calcium phosphate techniques (Graham et al., supra). Either the 293/E4 cell line on the 293/ORF6 cell line may be used.

Five days after transfection, the cell monolayer was harvested by freeze-thawing three times. The resulting hybrid virus was titered onto 293 cells and isolated plaques were picked. The process of plaque isolation was repeated twice more to ensure a single recombinant virus existed in the initial plaque stock. The plaque isolate stock was then amplified to a large viral stock according to standard virology techniques as described in Burlseson et al., *Virology: a Laboratory Manual*, Academic Press Inc. (1992).

Figure 2:
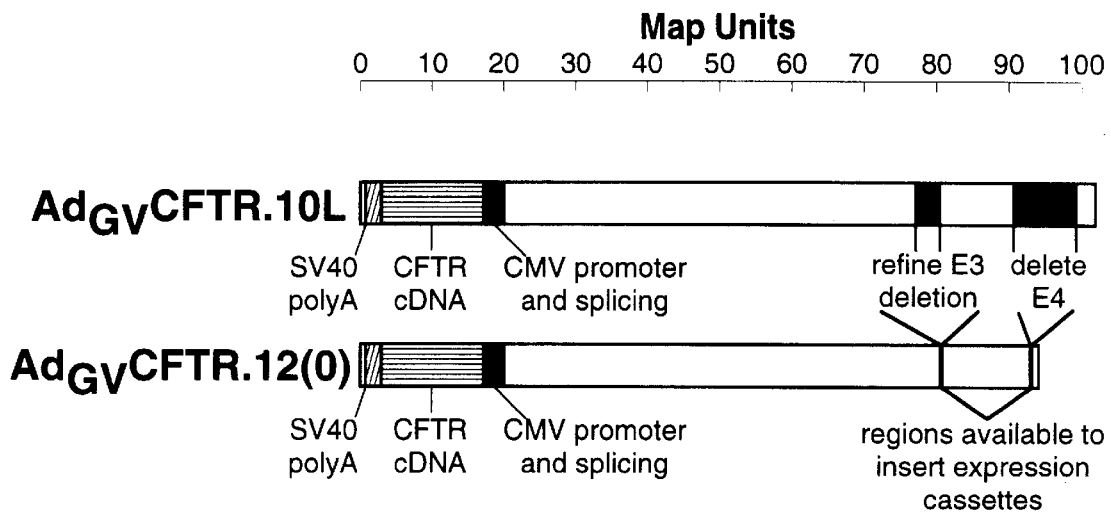
FIG. 2 is a schematic diagram of the $Ad_{GV}CFTR.11$ viral vector.

Since E4 contains essential gene products necessary for viral growth, the resulting E4 deletion mutant virus cannot grow in the absence of exogenously expressed E4. Therefore, all manipulations for viral construction are carried out in the new 293/E4 cell line or 293/ORF6 cell line (described in Example 6). The resulting virus is $Ad_{GV}$CFTR.11, which is represented schematically in FIG. 2, alone with $Ad_{GV}$CFTR.10L for comparison.

EXAMPLE 3

This example describes the generation of one embodiment of $Ad_{GV}.1^3$, i.e., $Ad_{GV}$CFTR.13, which is deficient in the E1, E2A, E3, and E4 regions.

$Ad_{GV}.13$ is characterized by not only complete elimination of E1 and E4 (as in $AD_{GV}.11$) but also complete elimination of E2A. The complete coding region of E2A is deleted by fusing together the DNA from two E2A mutant viruses, namely H5in800 and H5in804, containing insertions of Cla I restriction sites at both ends of the open reading frame (Vos et al., *Virology*, 172, 634–642 (1989); Brough et al., *Virology*, 190, 624–634 (1992)). The Cla I site of H5in800 is between codons 2 and 3 of the gene, and the Cla I site of H5in804 is within the stop codon of the E2A gene. The resultant virus contains an open reading frame consisting of 23 amino acids that have no similarity to the E2A reading frame. More importantly, this cassette offers yet another region of the virus genome into which a unique gene can be introduced. This can be done by inserting the gene of interest into the proper reading frame of the existing mini-ORF or by introducing yet another expression cassette containing its own promoter sequences, polyadenylation signals, and stop sequences in addition to the gene of interest.

Adenovirus DNA is prepared from H5in800 and H5in804. After digestion with the restriction enzyme Hin dIII (NEB), the Hin dIII A fragments from both H5in800 and H5in804 are cloned into pKS+ (Stratagene). The resulting plasmids are named pKS+H5in800Hin dIIIA and pKS+H5in804 Hin dIIIA, respectively. The Cla I (NEB) fragment from pKS+H5in800Hin dIIIA is then isolated and cloned in place of the identical Cla I fragment from PKS+H5in804Hin dIIIA. This chimeric plasmid, pHin dIIIA_E2A effectively removes all of the E2A reading frame as described above. At this point, the E2A deletion is moved at Bam HI (NEB) and Spe I (NEB) restriction sites to replace the wild-type sequences in pGV12(0) to construct pGV13(0).

Figure 3:
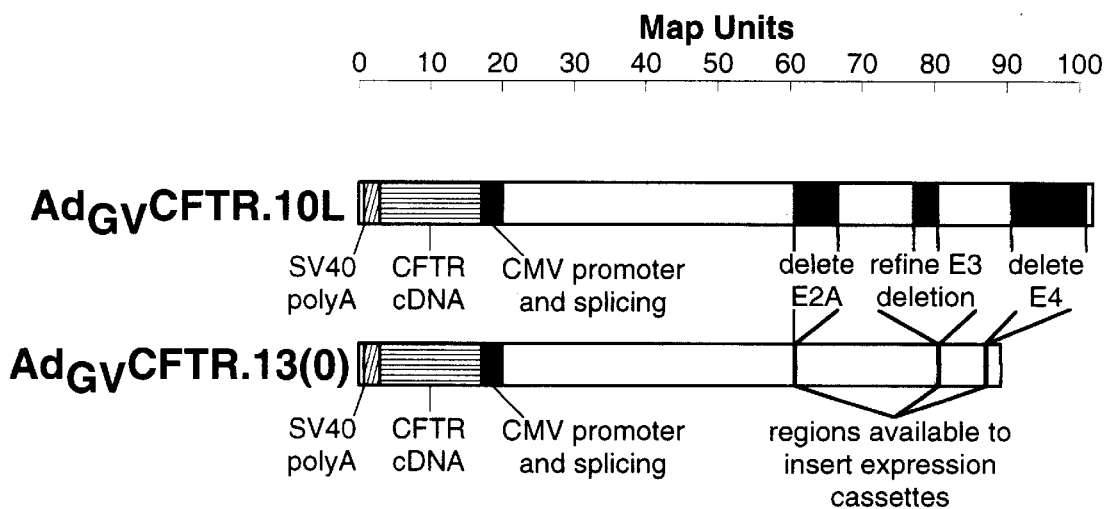
FIG. 3 is a schematic diagram of the $Ad_{GV}CFTR.13$ viral vector.

$Ad_{GV}$CFTR.13 virus (see FIG. 3) is constructed as previously described by using $Ad_{GV}$CFTR.10 left arm DNA and pGV13(0) right arm plasmid DNA. However, the recipient cell line for this virus construction is the triple complementing cell line 293/E4/E2A. FIG. 3 is a schematic diagram of the Ad$_{GV}$CFTR.13 viral vector. The diagram is aligned with that of Ad$_{GV}$CFTR.10L for comparison.

EXAMPLE 4

This example describes the generation of pGBSΔE3.

This plasmid was generated to remove the majority of the E3 region within PGBS, including the E3 promoter and existing E3 genes, to make room for other constructs and to facilitate introduction of E3 expression cassettes. This plasmid contains a deletion from 28331 to 30469.

A PCR fragment was generated with Ad5s(27324) and A5a(28330)X as primers and PGBS as template. The resulting fragment was digested with Eco RI (27331) and Xba I (28330) and gel-purified. This fragment was then introduced into PGBS at the Eco RI (27331) and Xba I (30470) sites.

EXAMPLE 5

This example describes the generation of pGBSΔE3ΔE4.

A large deletion of the Ad5 E4 region was introduced into pGBSΔE3 to facilitate moving additional exogenous sequences into the adenoviral genome. The 32830-35566 E4 coding sequence was deleted.

A Pac I site was generated in place of the Mun I site at 32830 by treating PGBS Mun I-digested DNA with Klenow to blunt-end the fragment and by ligating a Pac I linker to this. The modified DNA was then digested with Nde I and the resulting 1736 bp fragment (Nde I 31089 - Pac I 32830) was gel-purified. A PCR fragment was prepared using A5 (35564)P (IDT, Coralville, Iowa) and T7 primers (IDT, Coralville, Iowa) and pGBS as template. The resulting fragment was digested with Pac I and Sal I to generate Pac I 35566 - Sal I 35935. A Sma I site within the polylinker region of pUC 19 was modified to a Pac I site by ligating in a Pac I linker. The Pac I 35566 - Sal I 35935 fragment was moved into the modified pUC 19 vector at Pac I and Sal I sites, respectively, in the polylinker region. The modified Nde I 31089 - Pac I 32830 fragment was moved into the pUC 19 plasmid, into which the Pac I 35566 - Sal I 35935 fragment already had been inserted, at Nde I and Pac I sites, respectively. The Nde I 31089 - Sal I 35935 fragment from the pUC 19 plasmid was purified by gel purification and cloned in place of the respective Nde I and Sal I sites in pGBSΔE3 to yield pGBSΔE3ΔE4.

EXAMPLE 6

This example describes the generation of the 293/E4 cell line.

The vector pSMT/E4 was generated as follows. A 2752 bp Mun I (site 32825 of Ad2) - Sph I (polylinker) fragment was isolated from pE4(89-99), which is a pUC19 plasmid into which was subcloned region 32264-35577 from Ad2, blunt-ended with Klenow, and treated with phosphatase (NEB). The 2752 bp Mun I-Sph I fragment was then ligated into pMT010/A$^+$ (McNeall et al., Gene, 76, 81–89 (1989)), which had been linearized with Bam HI, blunt-ended with Klenow and treated with phosphatase, to generate the expression cassette plasmid, pSMT/E4.

The cell line 293 (ATCC CRL 1573; American Type Culture Collection, Rockville, Md.) was cultured in 10% fetal bovine serum Dulbecco's modified Eagle's medium (Life Technologies, Gaithersburg, Md.). The 293 cells were then transfected with pSMT/E4 linearized with Eco RI by the calcium phosphate method (Sambrook et al., Molecular Cloning: a Laboratory Manual, Cold Spring Harbor Laboratory Press (1989)). Approximately 24–48 hours post-transfection, medium (as above) containing 100 μM methotrexate and amethopterin (Sigma Chemical Co., St. Louis, Mo.) was added. The presence of methotrexate in the medium selects for expression of the dihydrofolate reductase (DHFR) gene, which is the selectable marker on the pSMT/E4 plasmid.

The normal cell DHFR gene is inhibited by a given concentration of methotrexate (cell type-specific), causing cell death. The expression of the additional DHFR gene in transfected cells containing pSMT/E4 provides resistance to methotrexate. Therefore, transfected cells containing the new genes are the only ones that grow under these conditions (for review, see Sambrook et al., supra).

When small colonies of cells formed from the initial single cell having the selectable marker, they were clonally isolated and propagated (for review, see Sambrook et al., supra). These clones were expanded to produce cell lines that were screened for expression of the product—in this case, E4—and screened for functionality in complementing defective viruses—in this case, both E1 and E4 defective viruses.

The result of this process produced the first 293/E4 cell lines capable of complementing adenoviral vectors defective in both E1 and E4 functions, such as Ad$_{GV}$CFTR.11.

EXAMPLE 7

This example describes the generation of the 293/E4/E2A cell line. The 293/E4/E2A cell line allows E1, E4, and E2A defective viral vectors to grow.

The E2A expression cassette (see FIG. 4) for introduction into 293/E4 cells is produced as follows. The first step is to alter surrounding bases of the ATG of E2A to make a perfect Kozak consensus (Kozak, J. Molec. Biol., 196, 947–950 (1987)) to optimize expression of E2A. Two primers are designed to alter the 5' region of the E2A gene. Ad5s(23884), an 18 bp oligonucleotide (5'GCCGCCTCATCCGCTTTT3') (SEQ ID NO:3), is designed to prime the internal region flanking the Sma I site of the E2A gene. DBP(ATG)R1, a 32 bp oligonucleotide (5'CCGGAATTCCACCAT-GGCGAGTCGGGAAGAGG3') (SEQ ID NO:4), is designed to introduce the translational consensus sequence around the ATG of the E2A gene modifying it into a perfect Kozak extended consensus sequence and to introduce an Eco RI site just 5' to facilitate cloning. The resulting PCR product using the above primers is digested with Eco RI and Sma I (NEB) and cloned into the identical polylinker sites of pBluescript IIKS+ (Stratagene, La Jolla, Calif.). The resulting plasmid is named pKS/ESDBP.

A Sma I-Xba I fragment is isolated from pHRKauffman (Morin et al., Mol. Cell. Biol., 9, 4372–4380 (1989)) and cloned into the corresponding Sma I and Xba I sites of pKS/ESDBP to complete the E2A reading frame. The resulting plasmid is named pKSDBP. In order to eliminate all homologous sequences from vector contained within the expression cassette, the Kpn I to Dra I fragment from pKSDBP is moved into corresponding Kpn I and Pme I sites in PNEB193 (NEB) in which the Eco RI sites in the polylinker have been destroyed (GenVec, Rockville, Md.). The resulting clone, pE2A, contains all of the E2A reading frame without any extra sequences homologous to the E2A deleted vector in Example 3.

A 5' splice cassette is then moved into pE2A to allow proper nuclear processing of the mRNA and to enhance expression of E2A further. To do this, pRK5, described in Example 1, is digested with Sac II (NEB), blunt-ended with Mung Bean nuclease (NEB), and digested with Eco RI (NEB). The resulting approx. 240 bp fragment of interest containing the splicing signals is cloned into the Cla I (blunt-ended with Klenow) to Eco RI sites of pE2A to generate p5'E2A. The blunt-ended (Klenow) Sal I to Hin dIII fragment from p5'E2A containing the E2A sequences is moved into the blunt-ended (Klenow) Xba I site of pSMT/puro and pSMT/neo. The resulting E2A is named pKSE2A.

The Xba I fragment from pKSE2A that contained all the E2A gene is moved into the Xba I site of pSMT/puro and pSMT/neo. The resulting E2A expression plasmids, pSMT/E2A/puro and pSMT/E2A/neo, are transfected into 293/E4 and 203/ORF-6 cells, respectively. Cells transfected with pSMT/E2A/puro are selected for growth in standard media plus puromycin, and cells transfected with pSMT/E2A/neo are selected for growth in standard media plus Geneticin (G418; Life Technologies, Gaithersburg, Md.). Clonal expansion of isolated colonies is as described in Example 6. The resulting cell lines are screened for their ability to complement E1, E4, and E2A defective viral vectors.

These cell lines are suitable for complementing vectors that are deficient in the E1, E4, and E2A regions of the virus, such as those described in the $Ad_{GV}$CFTR.13 series of viral vectors.

EXAMPLE 8

This example describes the generation of complementing cell lines using the cell line A549 (ATCC) as the parental line.

Ad2 virus DNA is prepared by techniques previously described. The genomic DNA is digested with Ssp I and Xho I, and the 5438 bp fragment is purified and cloned into Eco RV/Xho I sites of pKS+ (Stratagene) to produce pKS341-5778. After diagnostic determination of the clone, an Xho I (blunt-ended with Klenow) to Eco RI fragment is moved into Nru I (blunt) to Eco RI sites in pRC/CMVneo to produce PE1neo. Transformation of A549 cells with this clone yields a complementing cell line (similar to 293), wherein additional expression cassettes can be introduced, in a manner similar to that described for the 293 cell, to produce multicomplementing cell lines with excellent plaqueing potential.

EXAMPLE 9

This example sets forth a protocol for the generation of 293/E2A cell lines and use thereof to construct an adenoviral vector that is defective in both E1 and E2A regions.

Figure 4:
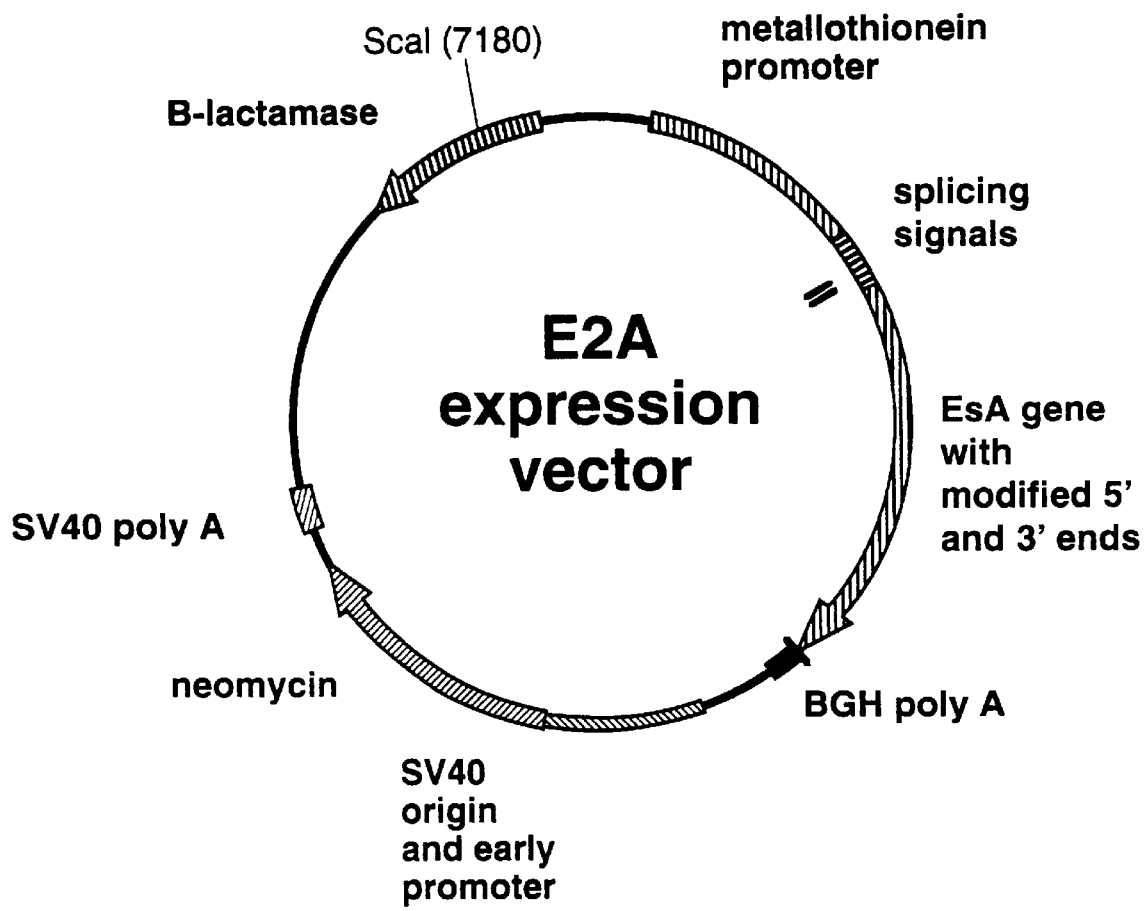
FIG. 4 is a schematic diagram of an E2A expression vector.

An E2A expression cassette vector was obtained, as described in Example 7 and depicted in FIG. 4. The E2A expression cassette vector includes the gene that confers neomycin resistance as a marker for transfected cells.

Also as described in Example 7, 293 cells were transfected with pSMT/E2A/neo and the transfected cells were selected for growth in standard media plus G418. Clonal expansion of the selected cells was effected as described in Example 6. The resulting cell lines were screened for their ability to express the DNA-binding protein (DBP; the product of the E2A gene) upon induction and their ability to complement E1 and E2A defective viral vectors.

For testing the ability of the neomycin positive (neo$^+$; i.e., resistant to neomycin) clonal isolates of the 293/E2A cell lines for their ability to express DBP, cells were grown in the presence of G418 to maintain selection. Established monolayers from independent clonal isolates were induced with 100 μM ZnCl$_2$ for 24 hours and the expression of the DBP gene was detected by immunoblotting, using a standard method. Of the 62 lines that were tested, 42% of the neo$^+$ cell lines were positive for DBP expression (DBP$^+$), and all of the DBP$^+$ cell lines showed inducible DBP expression. The following Table 1 presents the data from the DBP expression screen:

TABLE 1

| Cell line | DBP expression | Cell line | DBP expression |
| --- | --- | --- | --- |
| 3 | − | 202 | − |
| 6 | − | 203 | − |
| 9 | − | 207 | − |
| 10 | + | 208 | − |
| 12 | + | 210 | − |
| 13 | + | 211 | − |
| 16 | − | 212 | + |
| 17 | + | 213 | − |
| 19 | + | 215 | − |
| 21 | + | 216 | + |
| 32 | + | 219 | − |
| 35 | + | 301 | + |
| 36 | − | 302 | − |
| 39 | + | 305 | − |
| 41 | − | 307 | − |
| 42 | − | 309 | − |
| 43 | − | 311 | − |
| 52 | − | 313 | − |
| 54 | + | 314 | − |
| 55 | − | 315 | − |
| 57 | + | 316 | − |
| 58 | + | 317 | − |
| 60 | − | 321 | + |
| 61 | + | 323 | − |
| 62 | − | 324 | − |
| 104 | + | 325 | + |
| 107 | − | 326 | − |
| 108 | + | 327 | + |
| 111 | − | 328 | + |
| 112 | + | 329 | + |
| 201 | + | 330 | + |

Figure 5:
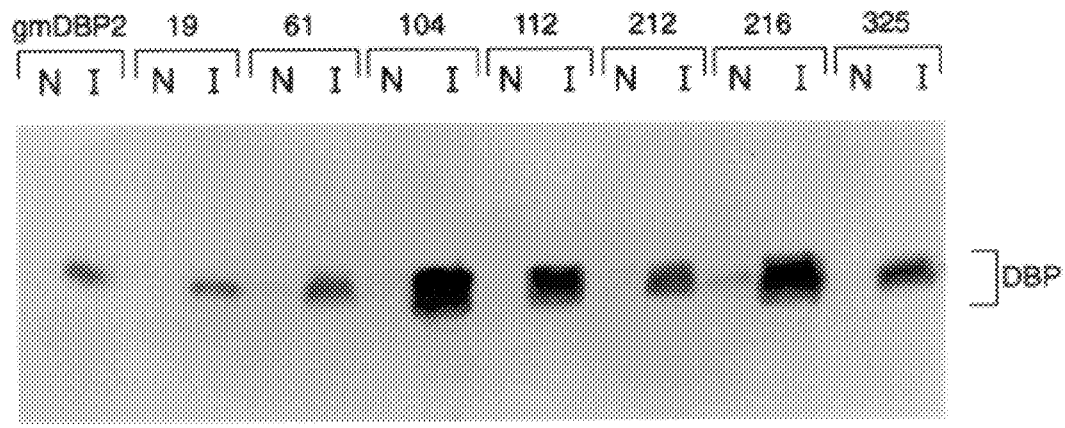
FIG. 5 is a representation of an immunoblot used to screen for the level of induced DBP expression in certain clonal 293/E2A cell lines.
Figure 6:
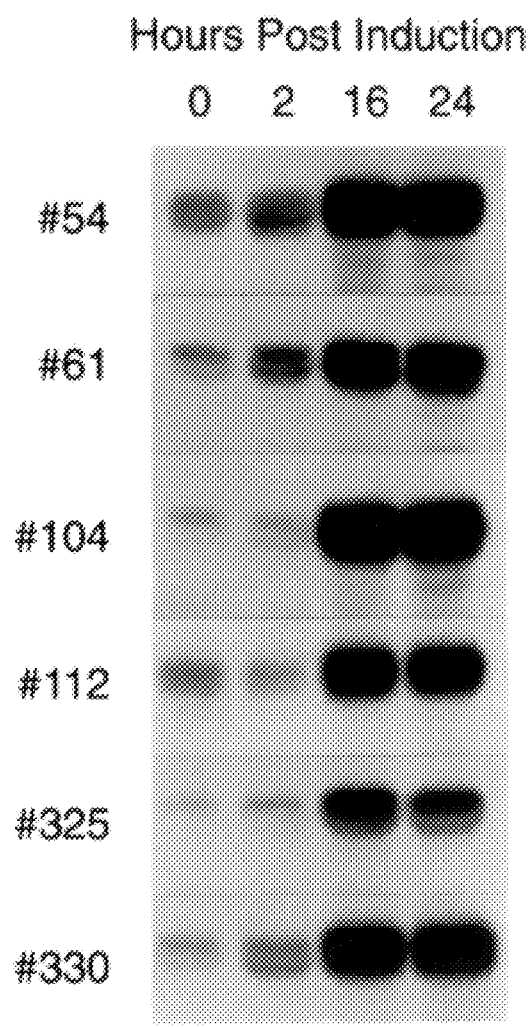
FIG. 6 is a representation of an immunoblot used to analyze the accumulation of DBP by certain clonal 293/E2A cell lines over the first 24 hours of induction.

The clonal 293/E2A cell lines were subsequently screened for the level of induced DBP expression via immunoblotting, using the method of Brough et al., supra, the results of which are depicted in the autoradiograms labelled as FIGS. 5 and 6. Those cell lines that accumulated a similar level of DBP as that in the HeLa-based gmDBP2 cells were further analyzed. As noted in FIG. 5, based on the lysates of induced cells, the level of induced DBP expression varied widely in the clonal isolates. For example, cell lines 104, 112, and 216 produced a substantial amount of DBP upon induction as described above, whereas cell lines 19 and 61 produced no more than that produced by gmDBP2 cells.

The clonal 293/E2A cell lines were also analyzed for their ability to accumulate DBP over the first 24 hours of induction, again using the method of Brough et al., supra. As noted in FIG. 6, based on lysates of cells harvested at 0, 2, 16, and 24 hours post-induction, several lines were noted to progressively accumulate DBP over the incubation period, consistent with virus growth.

For testing complementation by the resulting 293/E2A cell lines, E2A deletion virus was tested for growth on these cell lines using conventional techniques. As is well known in the art, viral growth can be measured semiquantitatively by simple observation of plaque formation in a monolayer of host cells, which was done here. The same lines were tested for their relative expression of the E2A gene, i.e., the relative expression of DBP was measured via immunoblot in accordance with Brough et al., Virology, 190, 624–634 (1992).

The relative level of expression or growth with respect to the aforementioned parameters (lowest +/− to highest +++++) of each of the cell lines tested is set forth in Table 2:

TABLE 2

| Cell Line | Relative level of DBP Expression | Ability to support an E2A deletion virus for plaque formation |
|---|---|---|
| 54 | ++++++ | +++++ |
| 61 | ++ | + |
| 104 | +++++ | − |
| 112 | ++++ | ++++++ |
| 201 | ++++ | ++ |
| 208 | − | − |
| 212 | +++ | + |
| 216 | ++++ | +/− |
| 325 | + | − |
| 327 | +++ | − |
| 328 | +++ | − |
| 330 | +++++ | − |

As reflected in Table 2, the result of this study showed that two 293/E2A cell lines (namely 54 and 112) support E2A deletion virus plaque formation and, thus, growth.

Figure 7:
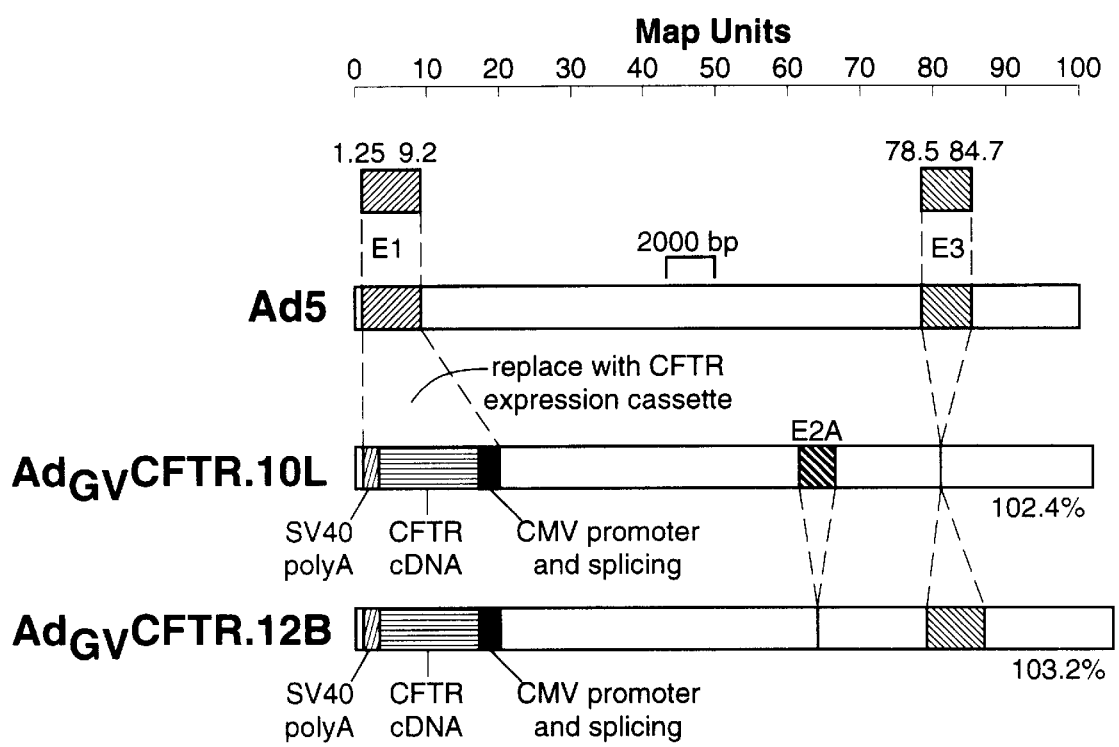
FIG. 7 is a set of schematic diagrams of the $Ad_{GV}CFTR.10L$ and $Ad_{GV}CFTR.12B$ viral vectors.

The selected cell lines were also shown to complement vectors that are deficient in the E1 and the E2A regions of the virus, using cell culturing methods that are routine to the art. Such a doubly deficient vector was generated using methods disclosed in Examples 1 and 2. FIG. 7 displays the structure of Ad$_{GV}$CFTR.12B, which is an adenoviral vector deficient for E1 and E2A regions. Presence of the Ad$_{GV}$CFTR.12B vector in three different lysates of transfected cells after passaging of the cells was noted by detecting the sequences of DNA associated with the vector via a standard PCR assay. The three different lysates were tested separately for the presence of CFTR sequences (columns labelled "A" in FIG. 8), absence of E2A sequences, i.e., evidence of the deletion (columns labelled "B"), and presence of wild-type E2A sequences (columns labelled "C"). The experiment can be analyzed from the reverse contrast photograph of the ethidium bromide-stained, gel-separated fragments of DNA depicted in FIG. 8, which was accomplished using standard methods.

Figure 8:
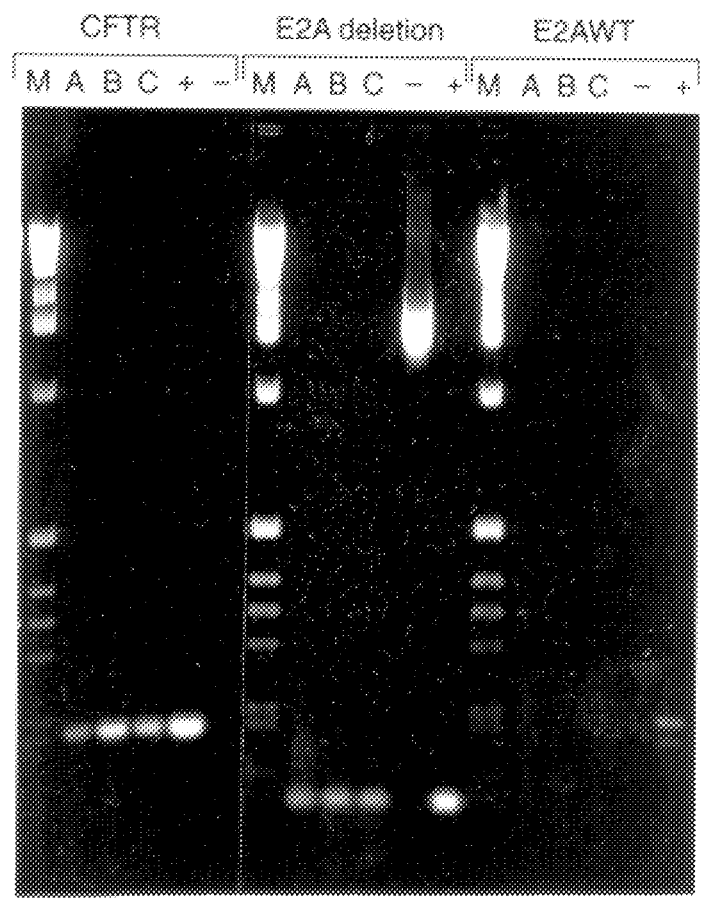
FIG. 8 is a photograph of a DNA gel stained with ethidium bromide, and provides data relating to the PCR detection of the $Ad_{GV}CFTR.12B$ viral vector from passaged transfection lysates.

The results show that all three lysates contain CFTR and E2A deletion sequences, which is consistent with the structure of the Ad$_{GV}$CFTR.12B vector. No wild-type E2A sequences could be detected in these lysates. In FIG. 8, "M" signifies a DNA marker to verify product size, "+" denotes a sample in which the positive template for the given primer set was used, "−" denotes a negative primer used for each given primer set, and, as noted above, A, B, and C stand for the three viral lysates tested.

Accordingly, an adenoviral vector having deletions at the E1 and E2A regions has been generated, and cell lines having the ability to complement the doubly deficient vector have been identified.

EXAMPLE 10

This example illustrates the use of an E2A deletion plasmid for the expression of a foreign DNA.

The E2A deletion plasmid pGV13(0), as described in Example 3, was used to construct a GV12B series of vectors. Modifications of the pGV13(0) included substituting a unique Sce I restriction site for the Cla I site and changing the region surrounding the ATG of the E2A gene to an optimized Kozak consensus sequence. A marker gene (β-glucuronidase) having flanking Sce I restriction sites was inserted in place of the E2A gene such that the marker gene expresses in response to all of the signals used to express the most abundant early gene, i.e., DBP. The resulting plasmid (pGBSE2GUS) was tested for functionality by transfection and subsequent assessment of β-glucuronidase activity; all transfected cell lines tested showed high levels of expression of β-glucuronidase, which is detected by the generation of a blue color when β-glucuronidase catalyzes a reaction with the substrate X-glu.

Figure 9:
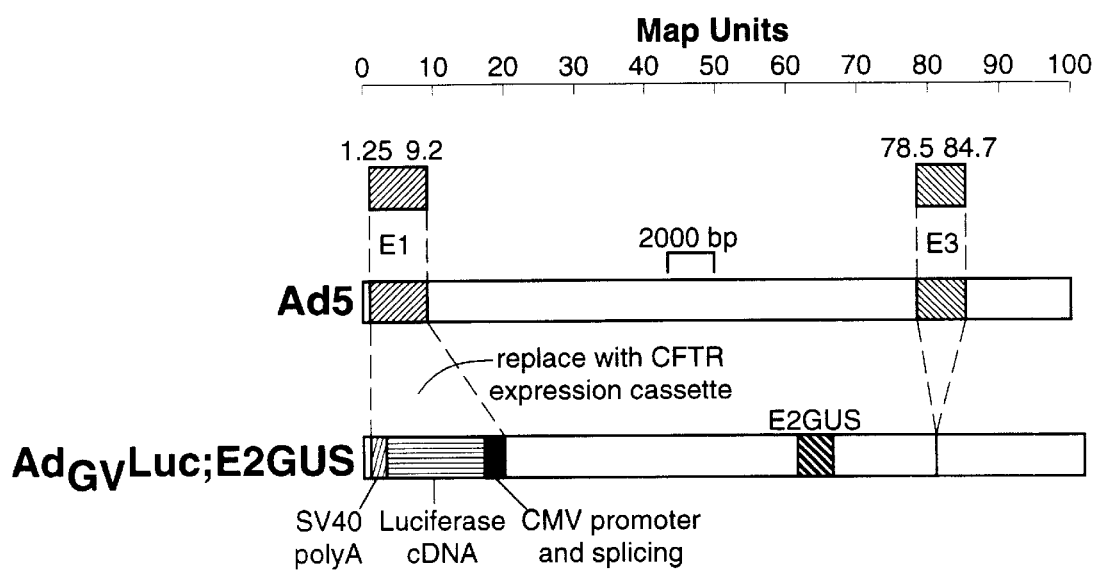
FIG. 9 is a schematic diagram of the $Ad_{GV}Luc;E2GUS$ viral vector.

Another viral vector (Ad$_{GV}$Luc;E2GUS), which is depicted in FIG. 9, was constructed to demonstrate the utility of the deleted E2 region for placement of a foreign DNA for gene therapy purposes, for example. The Ad$_{GV}$Luc;E2GUS vector contains the CMV luciferase marker in the E1 region and the E2 β-glucuronidase in the E2A region. The predecessor vector (Ad$_{GV}$LUC.10) was used to transfect 293/E2A cells; a subsequent staining of the resulting viral plaques for β-glucuronidase using X-glu revealed virtually no blue color, i.e., no β-glucuronidase activity was detected. Plaques that formed from 293/E2A cells transfected with the Ad$_{GV}$Luc;E2GUS vector generated a substantial amount of blue color upon the addition of X-glu.

Accordingly, a foreign DNA substituted at the E2A region of an adenoviral vector can function.

EXAMPLE 11

This example sets forth a protocol for the generation of 293/ORF6 cell lines and use thereof to construct an adenoviral vector that is defective in both E1 and E4 regions.

Figure 10:
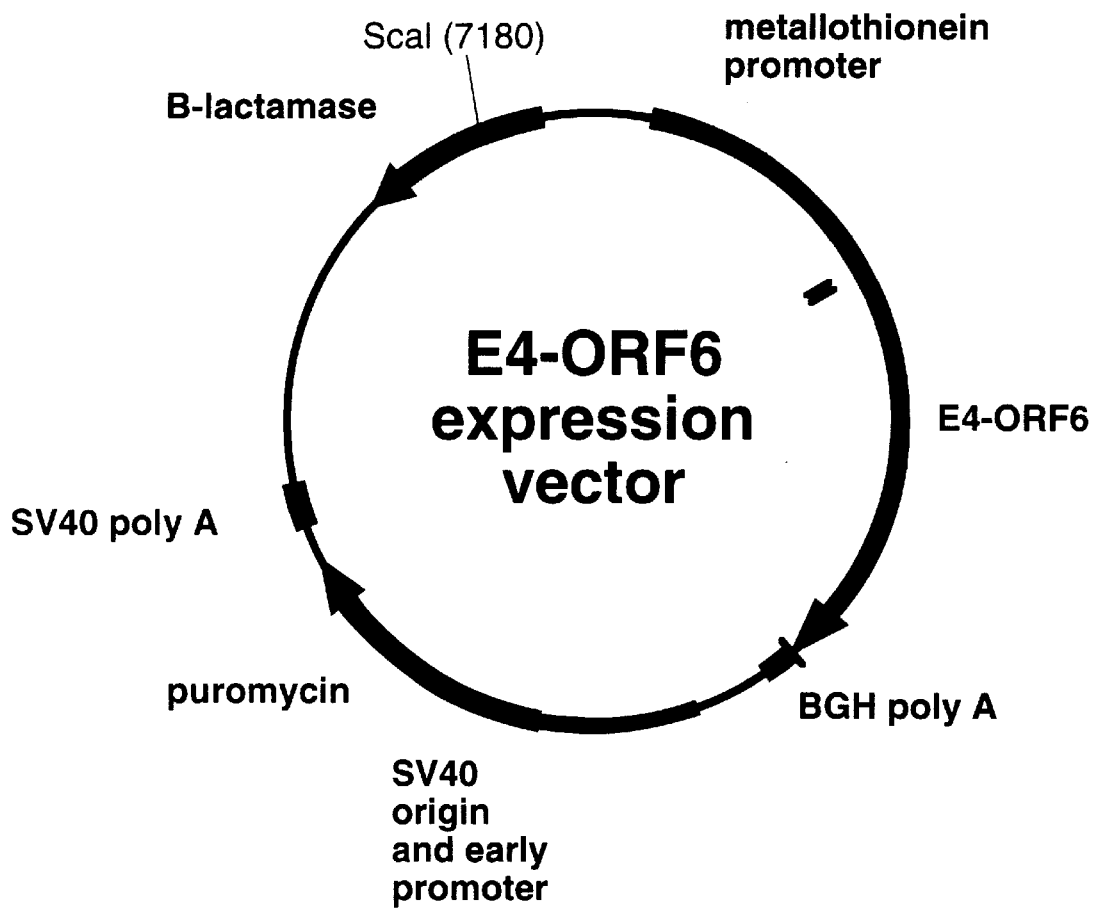
FIG. 10 is a schematic diagram of an E4-ORF6 expression vector.

The E4-ORF6 expression cassette depicted in FIG. 10 was constructed using the primers A5s(33190)P and A5a (34084)P in a polymerase chain reaction (PCR) (*PCR Protocols, A guide to Methods and Applications*, Innis et al., eds., Academic Press, Inc. (1990)) to amplify the ORF-6 gene of Ad5 E4 and generate Pac I sites at the ends for cloning. The amplified fragment was blunt-ended with Klenow and cloned into pCR-Script SK(+) (Stratagene, La Jolla, Calif.). The resulting plasmid, pCR/ORF-6, was sequenced and then the ORF-6 insert was transferred into the pSMT/puro expression vector, which was generated by ligation of a blunt-ended Eco RI - Hin dIII fragment containing the SMT promoter into the blunt-ended Mlu I-Hin dIII site in pRCpuro, to generate pSMT/ORF-6.

Transfection of 293 cells was effected with pSMT/ORF6/puro, and transfected cells were selected for growth in standard media plus puromycin. Clonal expansion was effected as described in Example 6. The resulting cell lines were screened for their ability to express E4-ORF6 upon induction and their ability to complement E1 and E4 defective viral vectors.

Puromycin resistant (puro$^+$; i.e., puromycin resistant) clonal isolates of the 293/ORF6 cell lines were screened for their ability to express ORF6. Cells were grown in the presence of puromycin to maintain selection. Established monolayers from independent clonal isolates were induced with 100 μM ZnCl$_2$ for 24 hours. The expression of the ORF6 gene was detected by Northern blotting, thereby identifying the RNA transcript. The relative level of expression (lowest (+) to highest (+++++)) of each of the cell lines tested is set forth in Table 3:

TABLE 3

| Cell line | ORF6 expression | Cell line | ORF6 expression |
|---|---|---|---|
| A2 | +++ | B8 | ++ |
| A2-1 | (+) | B8-1 | (+) |
| A2-2 | (+) | B8-2 | +++ |
| A2-3 | – | B8-3 | + |
| A2-4 | (+) | B8-4 | + |
| A2-5 | (+) | B8-5 | (+) |
| A2-6 | – | B8-6 | – |
| A2-7 | (+) | B8-7 | + |
| A2-8 | – | B8-8 | ++ |
| A2-9 | (+) | B8-9 | ++ |
| A2-10 | – | B8-10 | (+) |
| A2-11 | – | B8-14 | (+) |
| A2-12 | + | B8-16 | – |
| A2-13 | – | B8-18 | – |
| A2-14 | +++++ | B8-19 | – |
| A2-24 | – | B8-20 | – |
| A2-32 | ++++ | B8-21 | – |
| A2-59 | – | B8-23 | – |
| B8-22 | – | B8-27 | – |
| B8-24 | – | B8-27 | – |

The result of the test for expression of the ORF6 gene was that 53% of the puromycin-resistant cell lines were positive for ORF6 transcripts, and all such positive ORF6 cell lines were shown to be inducible for ORF6 expression.

Figure 11:
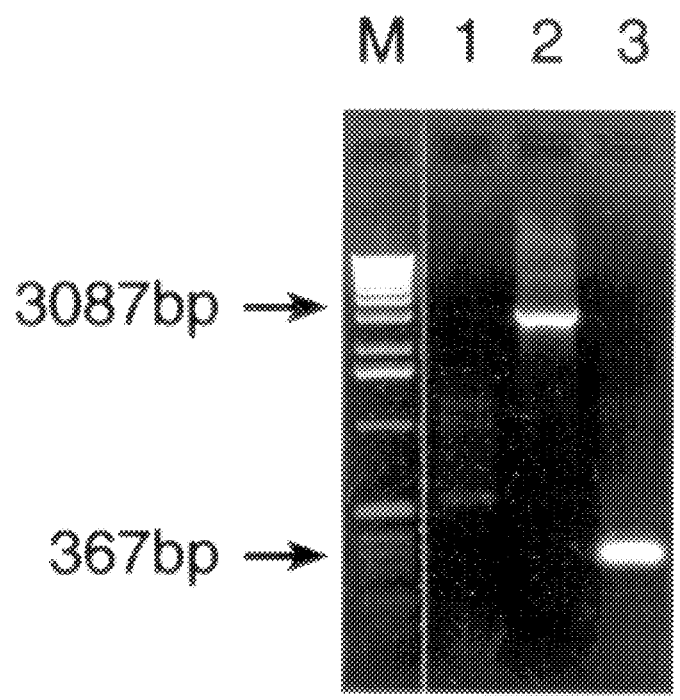
FIG. 11 is a photograph of a DNA gel stained with ethidium bromide, and provides data relating to the PCR detection of the E4 deletion region in passaged lysates of $Ad_{GV}\beta gal.11$.

PCR was also used to detect insertion of a gene at the E4 deletion region of an adenoviral vector, the results of which are depicted in FIG. 11. Passaged lysates of $Ad_{GV}\beta gal.11$ transfected cells were subjected to PCR that amplified certain gene sequences associated with wild-type E4, namely 3087 bp and 367 bp fragments. DNA from the lysates of mock infected 293/ORF6 cells (lane 1), $Ad_{GV}\beta gal.10$ infected cells (lane 2), and $Ad_{GV}\beta gal.11$ infected cells (lane 3) were subjected to gel electrophoresis and ethidium bromide staining. The photograph provided in FIG. 11, which is of the resulting stained gel, indicates that the $Ad_{GV}\beta gal.10$ vector is missing the portion of the E4 region that includes the 367 bp sequence and the $Ad_{GV}\beta gal.11$ vector is missing the portion of the E4 region that includes the 3087 bp sequence.

Figure 12:
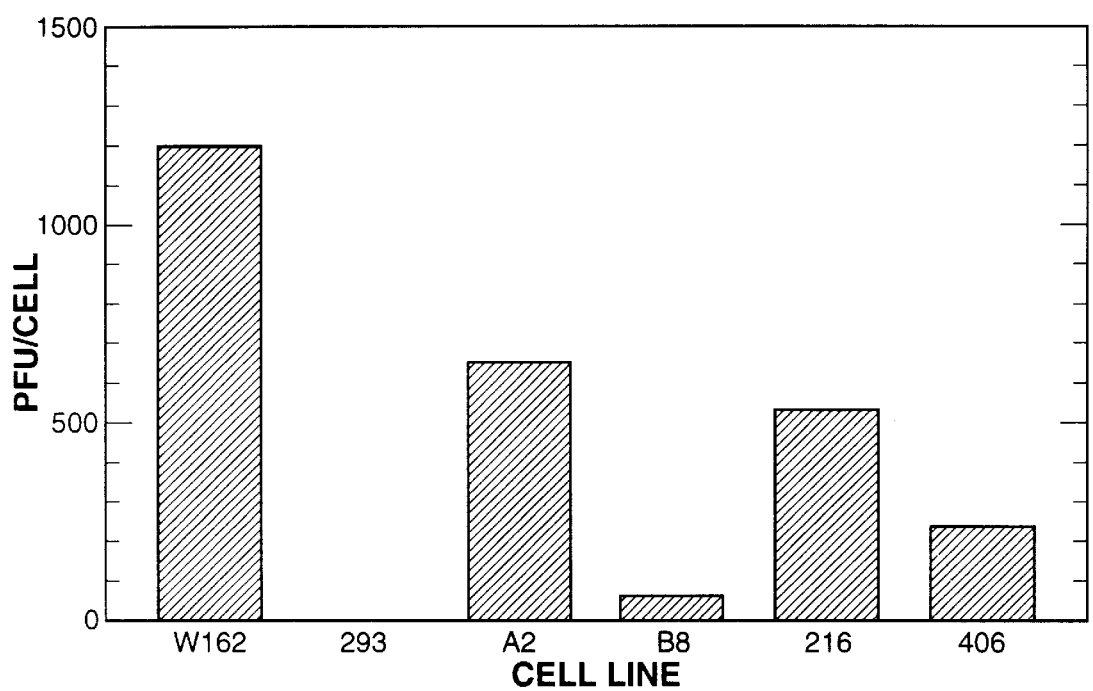
FIG. 12 is a bar graph depicting the amount of virus produced (PFU/cell y-axis) of an E4 deletion virus that retains E1 function after infection of different cell lines.

Growth of an E4 deleted vector was monitored in the 293/ORF6 cell lines. Cells were infected at a multiplicity of infection (moi) of 10, and the amount of virus growth was monitored by complementary plaque analysis after 5 days of growth. The results are depicted in FIG. 12, which is a bar graph that indicates the plaque forming units (PFU) per cell on the y-axis and identifies the cell line tested on the x-axis. For the positive control growth, the cell line W162 was used, which is a cell line that is known to complement E4 function. For the negative control, the 293 cell line was used, which is known to complement only for E1 function. Cell lines A2, B8, 216, and 406 are independent isolates of 293/ORF6 cell lines that show varying quantitative complementation of the E4 deletion virus (dl366). Specifically, the 293/ORF6 cell lines complement for E4 function.

Figure 13:
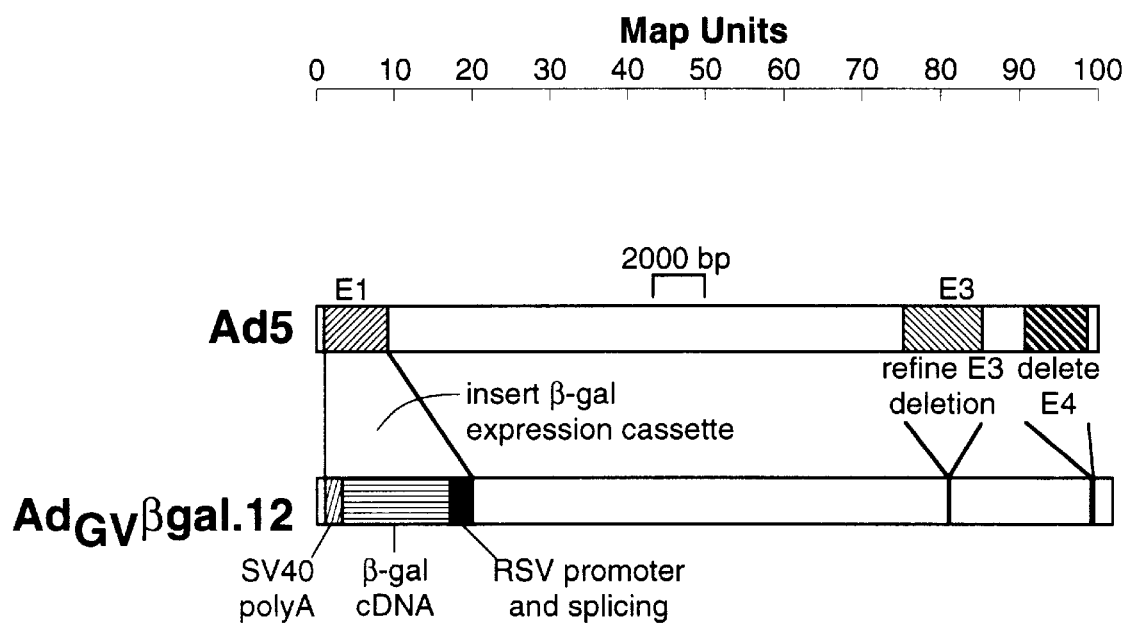
FIG. 13 is a schematic diagram of the $Ad_{GV}\beta gal.11$ viral vector.

Accordingly, cell lines have been identified that complement E4 function, thereby allowing growth of E4 deletion virus, which has been shown to be capable of harboring functioning foreign DNAs. These cell lines are suitable for complementing vectors that are doubly deficient for E1 and E4 regions of the virus, such as those described in the $Ad_{GV}CFTR.11$ series above or as shown in FIG. 13, which is a schematic representation of the $Ad_{GV}\beta$-gal.11 vector. The $Ad_{GV}\beta$-gal.11 vector has the β-galactosidase gene inserted at the E1 region and a deleted E4 region.

EXAMPLE 12

This example illustrates uses of adenoviral vectors having E1 and E4 deletions.

The E4 deletion plasmid, pGBSΔE4, has been modified to contain several unique restriction sites. These sites are used to clone any suitable foreign DNA into this region, using the adenoviral E4 promoter for expression. As noted above, cloning β-glucuronidase at this region resulted in a perfectly functional and foreign DNA expressing viral vector. Accordingly, a suitable foreign DNA placed at the E1 region and another suitable foreign DNA at the E4 region, both on the same viral vector, can express the respective foreign DNAs using the control of the E1 and E4 promoters or other promoters as desired.

A second modification of the E4 region allows for expression of a suitable foreign DNA from a variety of heterologous control elements. The plasmid construct was built in such a way so that multiple exchanges can be made conveniently. The multiplasmid pGV.11S contains the following features that can be exchanged conveniently:

1. an adenoviral segment used for homologous recombination, ligation to place the foreign DNA at either the E1 end or E4 end of the vector;
2. a promoter segment;
3. a splice signal segment;
4. a foreign DNA segment;
5. a poly adenylation segment;
6. the adenoviral packaging sequence;
7. the adenoviral ITR; and
8. all the plasmid DNA sequences necessary to select and grow the plasmid in bacteria as well as mammalian tissue culture.

EXAMPLE 13

This example describes the generation of one embodiment involving $Ad_{GV}.11S$, namely $Ad_{GV}CFTR.11S$, which comprises a spacer sequence inserted into the region of the E4 deletion present in $Ad_{GV}.11$. Similarly, the spacer can be incorporated into the region of the E4 deletion of, for instance, $Ad_{GV}.12S$ and $Ad_{GV}.13S$ to derive $Ad_{GV}CFTR.12S$ and $Ad_{GV}CFTR.13S$, respectively.

The $Ad_{GV}CFTR.11S$ recombinant virus was constructed, isolated and grown using the procedures described for the generation of $Ad_{GV}CFTR.11$ as described in Example 2. $Ad_{GV}CFTR.11S$ was constructed by means of a single in vivo recombination between 1–27082, i.e., the left arm, of $Ad_{GV}CFTR.10$ and the plasmid pGV11S, the right arm, linearized with Bam HI (NEB) and Sal I (NEB). Accordingly, the resultant $Ad_{GV}CFTR.11S$ vector is E1 and E4 deficient, and incorporates a spacer in the E4 deleted region as well as an SV40 polyadenylation sequence. Of course, the vector also contains the E4 polyadenylation sequence and the E4 promoter from the E4 region of the adenoviral genome.

Figure 14A:
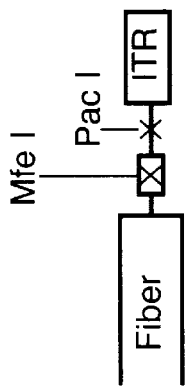
FIGS. 14A–C are schematic diagrams comparing the fiber/E4 region of vectors in which: E4 sequences are deleted entirely and the L5 fiber sequence is fused to the right-side ITR (FIG. 14A), E4 coding sequences are deleted and the L5 fiber sequence is fused to the E4 promoter and the right-side ITR to generate an $Ad_{GV}.11$ vector (FIG. 14B), and E4 coding sequences are deleted and sequences (including a SV40 polyadenylation sequence) have been added between the L5 fiber region and the right-side ITR to generate the $Ad_{GV}.11S$ based vector $Ad_{GV}CFTR.11S$ (FIG. 14C). Symbols: ITR, inverted terminal repeat; Mfe I (an isoschizomer of Mun I), Pac I, Eag I, palindromic recognition sites for these enzymes; GUS, β-glucuronidase coding sequence; SV40 polyA, simian virus 40 polyadenylation site; E4p, E4 promoter.
Figure 14B:
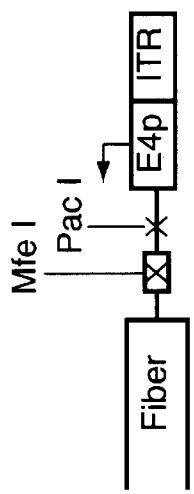
Figure 14C:
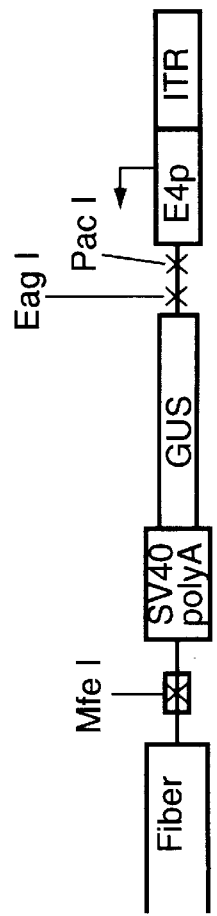

The fiber/E4 region of the $Ad_{GV}CFTR.11S$ vector is depicted in FIG. 14C. For comparative purposes, various other vectors according to the invention are depicted in FIGS. 14A and 14B. The vector in FIG. 14A is a complete E4 deletion fusing the L5 fiber to the right-side ITR. Such a vector comprises an approximate 2.5 kb deletion of the E4 region as compared with wild-type adenovirus. The various characteristics of $Ad_{GV}CFTR.11S$ (FIG. 14C) as compared with $Ad_{GV}.11$-based vectors (FIG. 14B), and other vectors, are described in the following examples.

EXAMPLE 14

This example describes a characterization of the growth behavior and production of fiber protein of an E1 and E4 deficient vector, as compared to a vector which is E1 deficient and retains the wild-type E4 region.

For these experiments, the E1 and E3 deficient $Ad_{GV}\beta gal.10$ vector and the E1 and E4 deficient vector $Ad_{GV}\beta gal.11$ were employed. The vectors were infected into the complementing 293/ORF-6 cell line. Immunoblot analysis was carried out on 293/ORF6 cell lysates as described in Example 9. In this experiment, rabbit serum directed against the whole adenovirus capsid was used. This antibody recognizes all of the structural proteins of the adenoviral capsid.

Figure 15:
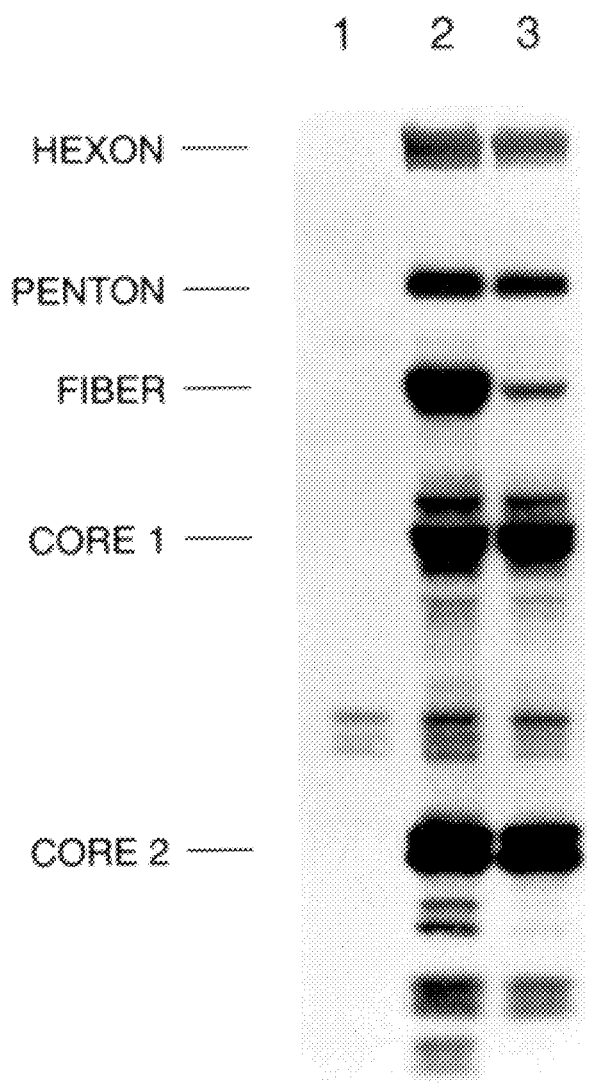
FIG. 15 is a representation of an immunoblot of various 293/ORF6 cell lysates infected with either no vector (i.e., mock infection) (lane 1), the E1 deficient $Ad_{GV}\beta gal.10$ vector (lane 2), or the E1 and E4 deficient vector $Ad_{GV}\beta gal.11$ (lane 3). The immunoblot was carried out using rabbit serum that recognizes all the structural proteins of the adenoviral capsid.

As illustrated in FIG. 15, the multiple replication deficient E1⁻ E4⁻ adenoviral vectors exhibited reduced fiber expression and reduced virus growth when compared to the singly replication deficient E1 deleted adenoviral vectors. Namely, there is a deficit in production of several late proteins, particularly fiber protein, in cells infected with a vector comprising deletions in E1 and E4 (i.e., an $Ad_{GV}\beta gal.11$ vector; lane 3), as compared with cells infected with an E1⁻ E4⁺ vector (i.e., an $Ad_{GV}\beta gal.10$ vector; lane 2). The reduction in fiber proteins in the E1⁻ E4⁻ vector corresponds to about 50-fold.

The effect on this deficit in terms of production of mature virions was examined by assessing the level of fiber protein present in purified capsids. Virus particles (capsids) were isolated over three sequential cesium chloride gradients using a standard vector production protocol. Immunoblot analysis using an antibody directed against adenovirus fiber protein was carried out after disruption of the capsids by boiling, and SDS/polyacrylamide gel electrophoresis.

Figure 16:
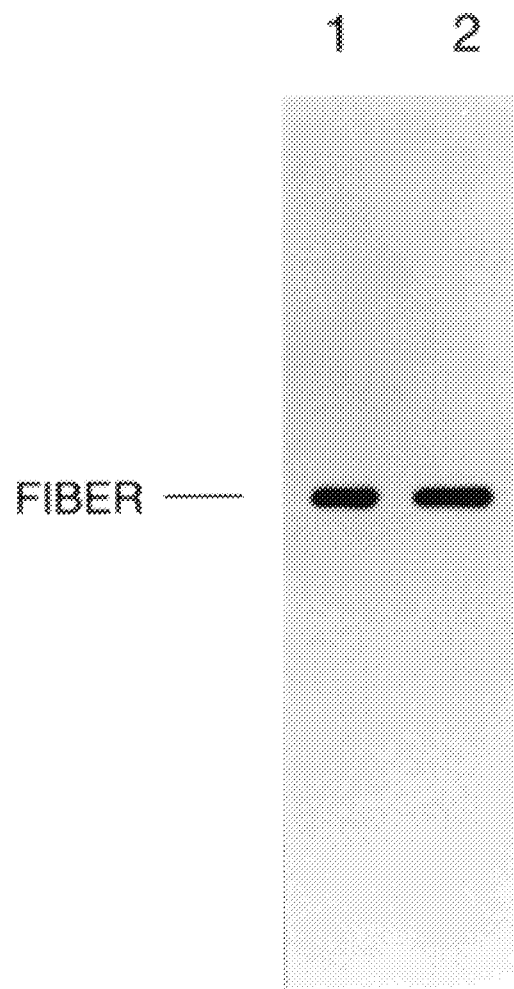
FIG. 16 is a representation of an immunoblot of purified capsids obtained from various 293/ORF6 cell lysates infected with either the E1 and E3 deficient $Ad_{GV}\beta gal.10$ vector (lane 1), or the E1 and E4 deficient vector $Ad_{GV}\beta gal.11$ (lane 2). The immunoblot was carried out using an antibody directed against adenoviral fiber protein.

The results of these experiments are depicted in FIG. 16. As can be seen from FIG. 16, similar levels of fiber protein are produced in cells infected with an E1 deficient vector (i.e., $Ad_{GV}\beta gal.10$, lane 1) as compared to cells infected with an E1⁻ E4⁻ vector (i.e., $Ad_{GV}\beta gal.11$, lane 2). Because the E1⁻ E4⁻ vector failed to produce levels of fiber protein approaching that of a singly replication deficient vector (in this case an E1⁻ vector), these results suggest that the reduced production of fiber protein causes a decrease in the total number of capsids that can be made in an infected cell.

EXAMPLE 15

This example describes the production of fiber protein observed upon infection of a cell with an E4 deficient vector comprising a spacer in the E4 region, as compared to infection of a cell with an E4 deficient vector that lacks such a spacer in the adenoviral genome.

For these experiments, the vectors employed, and the characterization thereof, was carried out as described in Example 14. Additionally, the E1 and E4 deficient $Ad_{GV}.11S$-based vector $Ad_{GV}CFTR.11S$ was examined. This vector further comprises an E3 deletion and a spacer inserted into the region of the E4 deletion present in $Ad_{GV}.11$, as described in Example 13.

Figure 17:
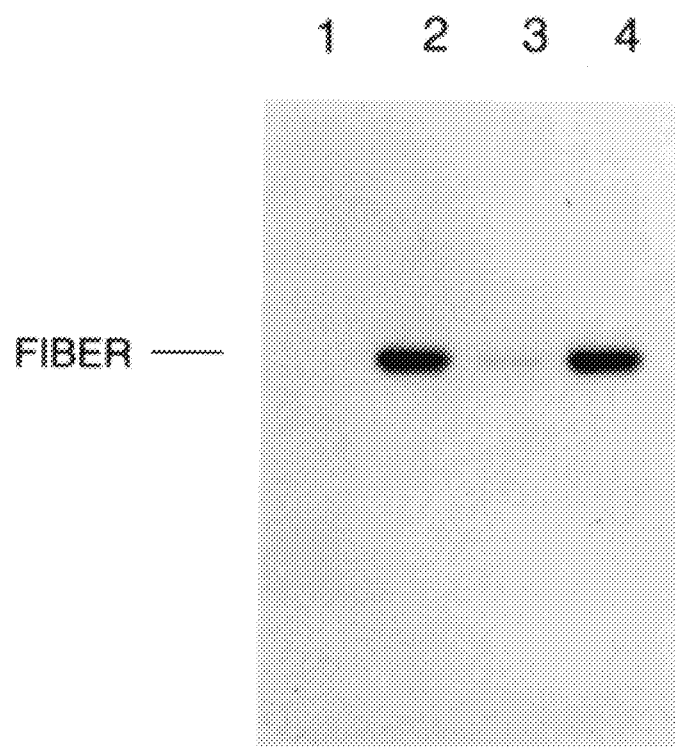
FIG. 17 is a representation of an immunoblot of various 293/ORF6 cell lysates infected with either no vector (i.e., mock infection) (lane 1), the E1 and E3 deficient $Ad_{GV}\beta gal.10$ vector (lane 2), the E1 and E4 deficient vector $Ad_{GV}\beta gal.11$ (lane 3), or the E1, E3 and E4 deficient $Ad_{GV}.11S$-based vector $Ad_{GV}CFTR.11S$ comprising a spacer in the region of the E4 deletion (lane 4). The immunoblot was carried out using an antibody directed against adenoviral fiber protein.

The results of these studies are illustrated in FIG. 17. As can be seen from FIG. 17, the incorporation of the spacer into the region of the E4 deletion enables levels of production of the L5 fiber protein approaching those obtained by a singly replication deficient adenoviral vector. Specifically, whereas fiber production was abrogated in a cell infected with the E1 and E4 deficient vector $Ad_{GV}\beta gal.11$ (lane 3), fiber levels observed for a cell infected with the multiply replication deficient E1⁻ E4⁻ vector comprising a spacer, i.e., $Ad_{GV}CFTR.11S$ (lane 4), approximated fiber levels observed for a cell infected with the singly replication deficient E1⁻ vector $Ad_{GV}\beta gal.10$ (lane 2).

These results thus confirm that incorporation of a spacer into an E1⁻ E4⁻ vector, particularly, into the region of the E4 deletion, provides for proper fiber production that is similar to that observed upon infection of a cell with a vector having only an E1 deletion.

EXAMPLE 16

This example describes the growth behavior of an E4 deficient vector comprising a spacer in the E4 region, as compared to an E4 deficient vector that lacks such a spacer in the adenoviral genome.

In these experiments, the ability to repair the growth defect of multiply deficient adenoviral vectors by addition of a spacer to at least one of the deleted regions was explored. Namely, production of active virus particles (focal forming units; ffu) per cell was examined as a function of time following infection of A232 cells with either the E1 and E3 deficient $Ad_{GV}.10$-based vector $Ad_{GV}\beta gal.10$, the E1 and E4 deficient $Ad_{GV}.11$-based vector $Ad_{GV}LacZ.11$, or the E1, E3 and E4 deficient $Ad_{GV}.11S$-based vector $Ad_{GV}CFTR.11S$ comprising a spacer sequence in the region of the E4 deletion. A232 cells were employed based on the ability of the cells of this line to produce E1 and E4 deletion viruses. A232 cells are 293/ORF6 cells that grow in standard medium and are induced to produce ORF6 after infection with 100 $\mu$M $ZnCl_2$. Focal forming units was determined by serially diluting and infecting virus stock onto complementing cell monolayers. The number of infected cells were counted by immunochemical detection using an antibody to the DBP or E2A gene product. Production of active virus particles was examined about 20, 40, 60 and 80 hours post-infection.

Figure 18:
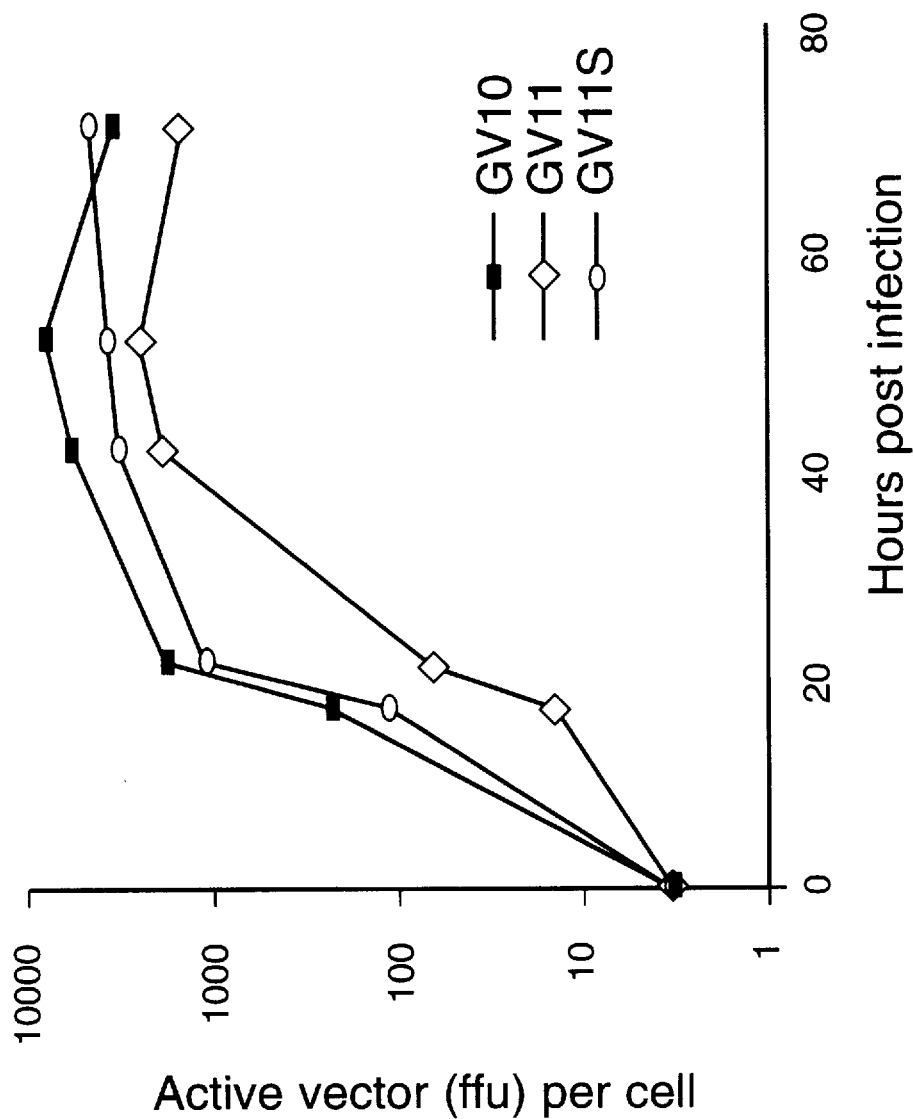
FIG. 18 is a graph of amount of active vector (focal forming units; ffu) per cell versus hours post infection for A232 cells infected with the E1 and E3 deficient Ad$_{GV}$.10-based vector Ad$_{GV}$βgal.10 (solid squares), the E1 and E4 deficient Ad$_{GV}$.11-based vector Ad$_{GV}$βgal.11 (open diamonds), or the E1, E3 and E4 deficient Ad$_{GV}$.11S-based vector Ad$_{GV}$CFTR.11S comprising a spacer in the region of the E4 deletion (open circles).

The results of these experiments are depicted in FIG. 18. There appears to be no kinetic difference between an E1 and E3 deficient $Ad_{GV}.10$ vector (solid squares) and an E1, E3 and E4 deficient $Ad_{GV}.11S$ vector comprising a spacer in the region of the E4 deletion (open circles). The worst virion production level is found with an E1, E3 and E4 deficient $Ad_{GV}.11$ vector which does not comprise a spacer (open diamonds) as can be seen by the 100 fold difference at 16 to 20 hours post-infection.

Additionally, production yield was determined. This involved the use of three cesium chloride gradients to purify the vector capsids. The virus must undergo a rigorous purification protocol for purification of vector capsids. As with any purification procedure, this results in a loss in total yield. Therefore, the critical data, in terms of the present experiments, is not the plateau point of the growth curves in FIG. 18, but rather the production level. Production yield (in active virus particles per cell) for cells infected with the various vectors is set out in Table 4.

TABLE 4

| Vector | Production Yield |
| --- | --- |
| $Ad_{GV} \cdot 10$ (i.e., $Ad_{GV}\beta gal \cdot 10$) | 650 |
| $Ad_{GV} \cdot 11$ (i.e., $Ad_{GV}\beta gal \cdot 11$) | 22 |
| $Ad_{GV} \cdot 11S$ (i.e., $Ad_{GV}CFTR \cdot 11S$) | 720 |

As illustrated by these data, upon incorporation of the spacer into a multiply replication deficient E1⁻ E4⁻ vector, the production of virus particles increases to (and perhaps exceeds) the viral production levels observed for a singly replication deficient E1 deleted vector.

Accordingly, these results confirm that the spacer sequence is able to counteract the growth defect and decreased fiber expression observed with an E1⁻ E4⁻ multiply replication deficient adenoviral vector. Moreover, considered in toto, the results validate that incorporation of this spacer into the genome of an adenovirus comprising E1 and E4 deletions, particularly incorporation into the region of the E4 deletion, provides for proper fiber production and increased viral growth similar to a singly replication deficient E1 deficient vector.

EXAMPLE 17

This example illustrates the characteristics of vectors comprising deletions in the E2 region, particularly the E2A region, of the adenoviral genome.

As observed with E4 mutants, the growth behavior of singly and multiply replication deficient adenoviruses comprising mutations in the E2A region is impaired. Accordingly, the ability of various E2A deletion mutants comprising wild-type E1 sequences to be complemented by cell lines according to this invention was examined. In particular, the previously described adenoviral vectors dl801, dl802, dl803 and dl807 comprising deletions in E2A (Rice et al., *J. Virol.*, 56, 767–778 (1985); Vos et al., *Virology*, 172, 634–632 (1988)) were studied.

The E2A open reading frame comprises from Ad5 nucleotide 22,443 to Ad5 nucleotide 24,032. The E2A gene product is a single-stranded DNA binding protein (i.e., DBP). The virus dl803 comprises a deletion of the E2A ORF from Ad5 nucleotide 22,542 to Ad5 nucleotide 23,816, and comprises the E2A ORF from Ad5 nucleotide 23,816 to Ad5 nucleotide 24,032. Consequently, the gene product of the dl803 E2A region (and variants thereof) comprises a chimeric protein consisting of a portion of the DBP protein that results from translation of the normal (i.e., wild-type) reading frame linked to further protein sequences that result from use of an alternate reading frame following the deletion. The region of the DBP protein that is lacking in the chimeric protein due to the deletion (i.e., the "Ct" region) has been implicated in DNA replication, ssDNA binding, and mRNA binding (Brough et al., *Virology*, 196, 269–281 (1993)). In comparison, the region retained, in part, by the vector (i.e., the "Nt" region) has been implicated in nuclear localization and late gene expression (Brough et al., supra).

The viruses dl801 and dl802 comprise modifications on the dl803 virus. Specifically, dl802 further comprises a deletion of the E2A ORF from Ad5 nucleotide 23,816 to Ad5 nucleotide 23,969 such that the resultant deletion virus comprises the E2A ORF from Ad5 nucleotide 23,969 to Ad5 nucleotide 24,032. Similarly, dl801 further comprises an in frame deletion of the E2A ORF from Ad5 nucleotide 23,816 to Ad5 nucleotide 24,011 such that the resultant deletion vector comprises the E2a ORF from Ad5 nucleotide 24,011 to Ad5 nucleotide 24,032. In comparison, dl807 comprises an in frame deletion of the E2A ORF from Ad5 nucleotide 23,882 to Ad5 nucleotide 23,954.

Figure 19:
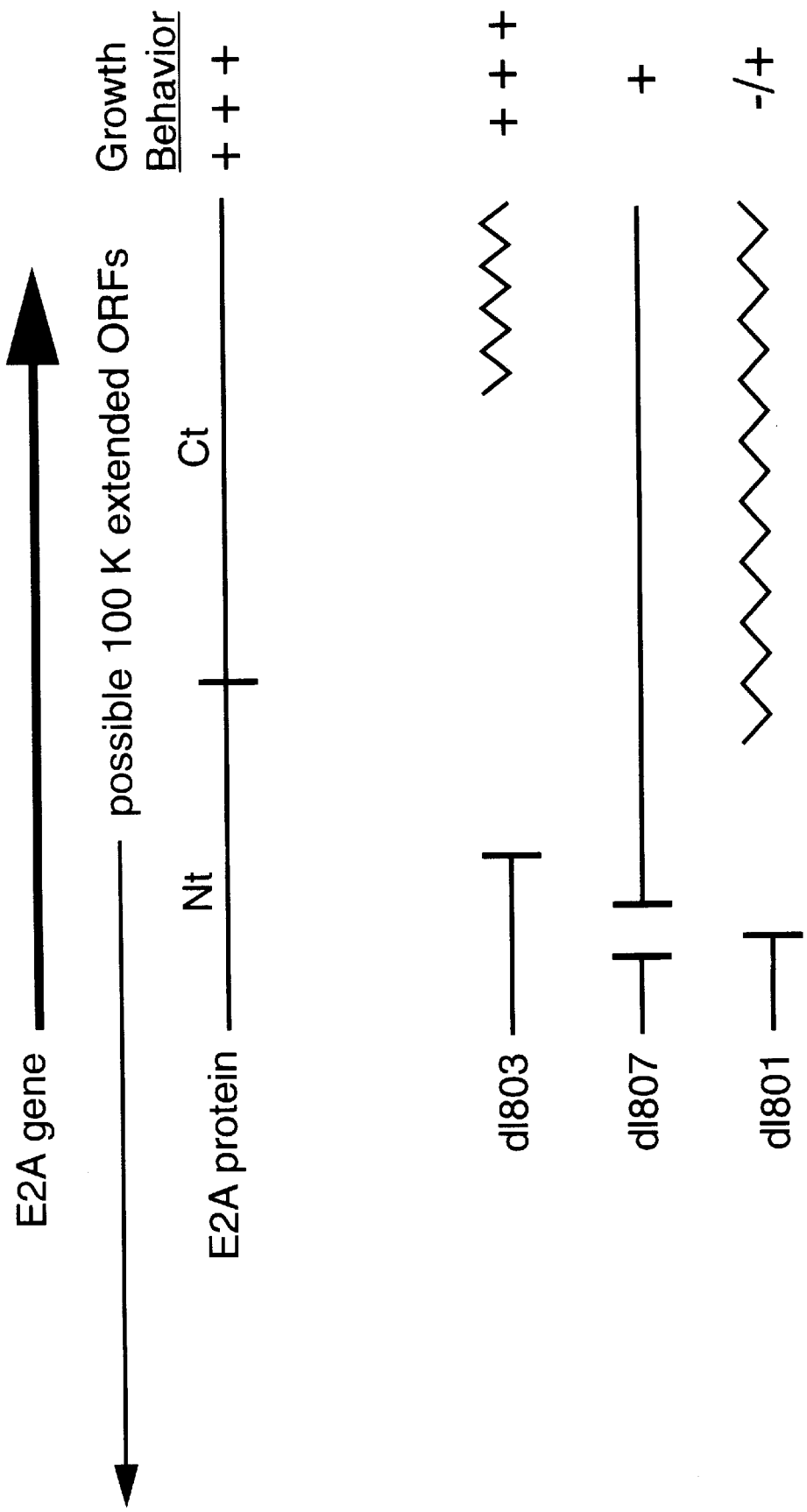
FIG. 19 is a schematic diagram of the E2a gene as translated into wild-type E2A protein, and the corresponding regions translated in the adenoviral deletion vectors dl801, dl802 and dl803, and the effect of such translation on growth behavior. Abbreviations and Symbols: Nt, region of the E2A gene product implicated in nuclear localization and late gene expression; Ct, region of the E2A gene product implicated in DNA replication, ssDNA binding, and mRNA binding; DBP, E2A gene product (i.e., single-stranded DNA binding protein); straight line, region of the E2A coding sequence that is translated in frame in the deletion vectors; jagged line, region of the E2A coding sequence that is translated out of frame in the deletion vectors as a consequence of the deletion of E2A sequences; +++, wild-type growth behavior; +, reduced viral growth; −/+, more severely reduced viral growth as evidenced by small plaques.

By study of the growth behavior of these various deletion vectors, it was discovered that certain segments of the E2A region of the adenoviral genome cannot be complemented and must be retained by (or added back into) an adenoviral vector to allow virus growth. The results of these experiments are summarized in FIG. 19. Specifically, the deletion mutant dl803 (which retains, in part, the Nt region, and lacks the wild-type Ct region) is fully functional and exhibits no growth deficit in the complementing E2A cell lines. In comparison, vectors dl807, dl802 (data not shown) and dl801 demonstrate a debilitated phenotype which cannot be complemented in E2A expressing cell lines. In particular, the dl801 vector exhibits a phenotype of extremely small plaques [−/+]. Therefore, these results confirm that the region remaining in dl803, comprising Ad5 nucleotide 23816 to Ad5 nucleotide 24032, is required for refinement of the E2A deletion and replication of E2A deletion vectors in currently available complementing cell lines.

All references, including publications and patents, cited herein are hereby incorporated by reference to the same extent as if each reference were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

---

What is claimed is:

1. An adenoviral vector comprising (a) an adenoviral genome deficient in the E4 region of the adenoviral genome,, (b) a spacer of at least 15 base pairs in the E4 region of the adenoviral genome, and (c) a passenger gene, wherein said spacer comprises a sequence that is non-native to the E4 region of the adenoviral genome, and wherein the viral production level of said adenoviral vector is greater than the viral production level of said adenoviral vector without said spacer.

2. The adenoviral vector of claim 1, wherein the viral production level of said adenoviral vector without said spacer and without said passenger gene is lower than the viral production level of said adenoviral vector without said spacer, said passenger gene, and said deficiency in the E4 region of the adenoviral genome.

3. A host cell comprising the adenoviral vector of claim 1.

4. A composition comprising the adenoviral vector of claim 1, and a carrier therefor.

5. A replication competent adenovirus-free stock of the adenoviral vector of claim 1, wherein said spacer comprises said passenger gene, wherein said adenoviral vector is prepared in a cell line which will support the growth of said adenoviral vector, and wherein the genome of said cell line is free of overlapping sequences with said adenoviral vector such that said cell genome will not mediate a recombination event which would produce a replication competent adenoviral vector.

6. A method of genetically modifying a cell in vitro, which comprises contacting said cell with the adenoviral vector of claim 1.

7. The adenoviral vector of claim 1, wherein said adenoviral genome is deficient in one or more essential gene functions of the E4 region of the adenoviral genome.

8. The adenoviral vector of claim 7, wherein said adenoviral genome is deficient in one or more essential gene functions of another region of the adenoviral genome.

9. The adenoviral vector of claim 8, wherein said another region is the E1 region of the adenoviral genome.

10. The adenoviral vector of claim 1, wherein said adenoviral genome is deleted of the E4 region of the adenoviral genome.

11. The adenoviral vector of claim 10, wherein said adenoviral genome is deficient in one or more other essential gene functions of another region of the adenoviral genome.

12. The adenoviral vector of claim 1, wherein said adenoviral genome is deleted of the E4 region of the adenoviral genome except the E4 promoter and the E4 polyadenylation sequence.

13. The adenoviral vector of claim 12, wherein said adenoviral genome is deficient in one or more other essential gene functions of another region of the adenoviral genome.

14. The adenoviral vector of claim 1, wherein said adenoviral genome is deleted of the E4 region of the adenoviral genome except the E4 polyadenylation sequence.

15. The adenoviral vector of claim 14, wherein said adenoviral genome is deficient in one or more essential gene functions of another region of the adenoviral genome.

16. The adenoviral vector of claim 1, wherein said adenoviral genome is further deficient in the E2A region of the adenoviral genome.

17. The adenoviral vector of claim 16, wherein said E2A region comprises a portion of the adenoviral genome which encodes amino acids of the Nt domain of the DBP sufficient to allow for viral production, and wherein said E2A region is deficient in the portion of the adenoviral genome which encodes amino acid sequences of the Ct domain that are necessary for DNA binding.

18. The adenoviral vector of claim 1, wherein said spacer is about 100 to about 12,000 base pairs.

19. A method of genetically modifying a cell in vitro, which comprises contacting said cell with the adenoviral vector of claim 18.

20. The adenoviral vector of claim 18, wherein said spacer is about 500 to about 8,000 base pairs.

21. The adenoviral vector of claim 20, wherein said spacer is about 1,500 to about 6,000 base pairs.

22. The adenoviral vector of claim 1, wherein said spacer comprises a polyadenylation sequence other than an E4 adenoviral polyadenylation sequence.

23. The adenoviral vector of claim 22, wherein said spacer comprises an SV40 polyadenylation sequence.

24. A method of genetically modifying a cell in vitro, which comprises-contacting said cell with the adenoviral vector of claim 22.

25. A replication competent adenovirus-free stock of the adenoviral vector of any of claims 1, 2 and 7–17, wherein said spacer comprises a polyadenylation sequence other than an E4 adenoviral polyadenylation sequence.

26. The replication competent adenovirus-free stock of claim 25, wherein said spacer comprises an SV40 polyadenylation sequence.

27. A replication competent adenovirus-free stock of the adenoviral vector of claim 1, wherein said spacer comprises a polyadenylation sequence other than an E4 adenoviral polyadenylation sequence, wherein said adenoviral vector is prepared in a cell line which will support the growth of said adenoviral vector, and wherein the genome of said cell line is free of overlapping sequences with said adenoviral vector such that said cell genome will not mediate a recombination event which would produce a replication competent adenoviral vector.

28. The replication competent adenovirus-free stock of claim 27, wherein said spacer comprises an SV40 polyadenylation sequence.

29. A replication competent adenovirus-free stock of the adenoviral vector of any of claims 1, 2 and 7–17, wherein said spacer comprises a polyadenylation sequence other than an E4 adenoviral polyadenylation sequence, wherein said adenoviral vector is prepared in a cell line which will support the growth of said adenoviral vector.

30. The replication competent adenovirus-free stock of claim 29, wherein said spacer comprises an SV40 polyadenylation sequence.

31. A replication competent adenovirus-free stock of the adenoviral vector of any of claims 1, 2 and 7–17, wherein said spacer comprises said passenger gene, wherein said adenoviral vector is prepared in a cell line which will support the growth of said adenoviral vector.

32. A method of increasing the propagation in a complementing cell line of an adenoviral vector comprising (a) an adenoviral genome deficient in the E4 region and (b) a passenger gene, which method comprises incorporating into the E4 region of the adenoviral genome of said adenoviral vector a spacer comprising at least about 15 base pairs, wherein said spacer comprises a sequence that is non-native to the E4 region of the adenoviral genome, thereby resulting in an increase in the viral production level of said adenoviral vector.

33. The method of claim 32, wherein said adenoviral genome is deficient in one or more essential gene functions of another region of the adenoviral genome.

34. The method of claim 32, wherein said adenoviral genome is deficient in one or more essential gene functions of the E4 region of the adenoviral genome.

35. The method of claim 34, wherein said adenoviral genome is deficient in one or more essential gene functions of another region of the adenoviral genome.

36. The method of claim 34, wherein said adenoviral genome is further deficient in at least one or more essential gene functions of the E1 region of the adenoviral genome.

37. The method of claim 32, wherein said adenoviral genome is deleted of all the open reading frames of the E4 region of the adenoviral genome.

38. The method of claim 37, wherein said adenoviral genome is deficient in one or more essential gene functions of another region of the adenoviral genome.

39. The method of claim 32, wherein said adenoviral genome is deleted of the E4 region of the adenoviral genome except the E4 promoter and the E4 polyadenylation sequence.

40. The method of claim 39, wherein said adenoviral genome is deficient in one or more essential gene functions of another region of the adenoviral genome.

41. The method of claim 39, wherein said adenoviral genome is deleted of the E4 region of the adenoviral genome except the E4 polyadenylation sequence.

42. The method of claim 32, wherein said spacer is about 100 to about 12,000 base pairs.

43. The method of claim 42, wherein said spacer is about 500 to about 8,000 base pairs.

44. The method of claim 42, wherein said spacer is about 1,500 to about 6,000 base pairs.

45. The method of claim 32, wherein said spacer comprises a polyadenylation sequence other than an E4 adenoviral polyadenylation sequence.

46. The method of claim 45, wherein said spacer comprises an SV40 polyadenylation sequence.

47. An adenoviral vector comprising a portion of the E2A region of the adenoviral genome which encodes amino acids of the Nt domain of the DBP sufficient to allow for viral production, and wherein said E2A region is deficient in the portion of the adenoviral genome which encodes amino acid sequences of the Ct domain that are necessary for DNA bindings and further wherein the adenoviral vector comprises a passenger gene.

48. The adenoviral vector of claim 47, wherein said adenoviral genome is deficient in one or more essential gene functions of another region of the adenoviral genome.

49. An adenoviral vector comprising (a) an adenoviral genome deficient in the E4 region of the adenoviral genome, and (b) a spacer of at least 15 base pairs in the E4 region of the adenoviral genome, wherein said spacer comprises a passenger gene that is non-native to the E4 region of the adenoviral genome, and wherein the viral production level of said adenoviral vector is greater than the viral production level of said adenoviral vector without said spacer.

50. The adenoviral vector of claim 49, wherein said adenoviral genome is deficient in one or more essential gene functions of the E4 region of the adenoviral genome.

51. The adenoviral vector of claim 49, wherein the viral production level of said adenoviral vector without said spacer and without said passenger gene is lower than the viral production level of said adenoviral vector without said spacer, said passenger gene, and said deficiency in the E4 region of the adenoviral genome.

52. The adenoviral vector of claim 50, wherein said adenoviral genome is deficient in one or more essential gene functions of another region of the adenoviral genome.

53. The adenoviral vector of claim 52, wherein said another region is the E1 region of the adenoviral genome.

54. The adenoviral vector of claim 52, wherein said adenoviral genome is deleted of the E4 region of the adenoviral genome.

55. The adenoviral vector of claim 54, wherein said adenoviral genome is deficient in one or more other essential gene functions of another region of the adenoviral genome.

56. The adenoviral vector of claim 52, wherein said adenoviral genome is deleted of the E4 region of the adenoviral genome except the E4 promoter and the E4 polyadenylation sequence.

57. The adenoviral vector of claim 56, wherein said adenoviral genome is deficient in one or more other essential gene functions of another region of the adenoviral genome.

58. The adenoviral vector of claim 49, wherein said adenoviral genome is deleted of the E4 region of the adenoviral genome except the E4 polyadenylation sequence.

59. The adenoviral vector of claim 50, wherein said adenoviral genome is deficient in one or more essential gene functions of another region of the adenoviral genome.

60. The adenoviral vector of claim 49, wherein said adenoviral genome is further deficient in the E2A region of the adenoviral genome.

61. The adenoviral vector of claim 60, wherein said E2A region comprises a portion of the adenoviral genome which encodes amino acids of the Nt domain of the DBP sufficient to allow for viral production, and wherein said E2A region is deficient in the portion of the adenoviral genome which encodes amino acid sequences of the Ct domain that are necessary for DNA binding.

62. A replication competent adenovirus-free stock of the adenoviral vector of any of claims 49–61.

63. A method of increasing the propagation in a complementing cell line of an adenoviral vector comprising an adenoviral genome deficient in the E4 region, which method comprises incorporating into the E4 region of the adenoviral genome of said adenoviral vector a spacer comprising at least about 15 base pairs, wherein said spacer comprises a passenger gene that is non-native to the E4 region of the adenoviral genome, thereby resulting in an increase in the viral production level of said adenoviral vector.

* * * * *